(12) United States Patent
Nakano et al.

(10) Patent No.: US 7,929,135 B2
(45) Date of Patent: Apr. 19, 2011

(54) METHOD AND APPARATUS FOR DETECTING SIZE OF PARTICLES IN LIQUID

(75) Inventors: Koichi Nakano, Hyogo (JP); Yasuhiro Hayashi, Hyogo (JP)

(73) Assignee: Hokuto Electronics Incorporated, Nishinomiya (JP)

( * ) Notice: Subject to any disclaimer, the term of this patent is extended or adjusted under 35 U.S.C. 154(b) by 0 days.

(21) Appl. No.: 12/774,545

(22) Filed: May 5, 2010

(65) Prior Publication Data

US 2010/0231908 A1    Sep. 16, 2010

Related U.S. Application Data

(63) Continuation of application No. PCT/JP2008/002980, filed on Oct. 21, 2008.

(51) Int. Cl.
*G01N 15/02* (2006.01)
(52) U.S. Cl. .......................................... 356/335
(58) Field of Classification Search ........... 356/335–342
See application file for complete search history.

(56) References Cited

U.S. PATENT DOCUMENTS

| | | | | |
|---|---|---|---|---|
| 5,684,583 A | * | 11/1997 | Abe et al. | 356/335 |
| 6,522,405 B2 | | 2/2003 | Sakamoto et al. | |
| 2002/0044281 A1 | | 4/2002 | Sakamoto et al. | |
| 2007/0143504 A1 | | 6/2007 | Yoshida | |

FOREIGN PATENT DOCUMENTS

| | | |
|---|---|---|
| JP | 61-10743 A | 1/1986 |
| JP | 2001-281135 A | 10/2001 |
| JP | 3301658 B2 | 7/2002 |
| JP | 3745947 B2 | 2/2006 |
| JP | 2007-172087 A | 7/2007 |
| JP | 2009-8602 A | 1/2009 |

OTHER PUBLICATIONS

"Technology for simplifying particle control in fluid in real time" vol. 16, No. 10, pp. 68-71, Oct. 2006.
Japanes Official Communication dated Oct. 6, 2009 for corresponding Japanese Patent Application 2009-531688.

* cited by examiner

*Primary Examiner* — Michael P Stafira
(74) *Attorney, Agent, or Firm* — Birch, Stewart, Kolasch & Birch, LLP

(57) ABSTRACT

The size of particles is detected accurately and at low cost even when there are few microparticles as impurities included in a liquid. Provided is a method of detecting a size of particles in a liquid by detecting diffraction fringes appearing due to the particles in the liquid by a light detection portion. Diffraction fringes are detected by a first light detection portion and a second light detection portion that are separated along the flow direction of the liquid. A peak time difference (T2) that is a difference between times at which peak values appear in a detection signal from the first and second light detection portion is measured, and an area (SQ) based on the waveform of the detection signal is measured. The sizes of the particles included in the liquid are detected based on the peak time differences (T2) and the areas (SQ) that were measured.

18 Claims, 26 Drawing Sheets

FIG. 12

| PARTICLE SIZE | NUMBER CONCENTRATION (pls/ml) | MEASUREMENT TIME (min.) | NUMBER IN THE 1ST AREA | NUMBER IN THE 2ND AREA | NUMBER IN THE 3RD AREA | TOTAL SUM |
|---|---|---|---|---|---|---|
| 150nm | 7800 | 10 | 2915.0 | 93.0 | 4.0 | 3012 |
| 200nm | 2700 | 10 | 2603.0 | 404.0 | 6.0 | 3013 |
| 300nm | 580 | 10 | 1232.0 | 1522.0 | 256.0 | 3010 |
| 400nm | 390 | 10 | 644.0 | 880.0 | 1484.0 | 3008 |

DKI

| SIZE [nm] | NUMBER CONCENTRATION [pls/ml] | AREA 3 [pls/10min.] | AREA 2 [pls/10min.] | AREA 1 [pls/10min.] | EACH AREA Σ [pls/10min.] |
|---|---|---|---|---|---|
| 400 | Na | P3a | P2a | P1a | P123a |
|  | 1000 | 300 | 700 | 2500 | 3500 |
| 300 | Nb | P3b | P2b | P1b | P123b |
|  | 2000 | 700 | 2500 | 800 | 4000 |
| 200 | Nc | P3c | P2c | P1c | P123c |
|  | 5000 | 2000 | 800 | 200 | 3000 |
|  |  | P3abc | P2abc | P1abc | P123abc |
|  |  | 3000 | 4000 | 3500 | 10500 |

| SIZE [nm] | NUMBER CONCENTRATION [pls/ml] | AREA 3 [pls/10min.] | AREA 2 [pls/10min.] | AREA 1 [pls/10min.] | EACH AREA Σ [pls/10min.] |
|---|---|---|---|---|---|
| | | X3abc | X2abc | X1abc | X123abc |
| | | 1370 | 1610 | 1170 | 4150 |
| 400 | XNa | X3a | X2a | X1a | X123a |
| | ? | ? | ? | ? | ? |
| 300 | XNb | X3b | X2b | X1b | X123b |
| | ? | ? | ? | ? | ? |
| 200 | XNc | X3c | X2c | X1c | X123c |
| | ? | ? | ? | ? | ? |

| SIZE [nm] | NUMBER CONCENTRATION [pls/ml] | AREA 3 [pls/10min.] | AREA 2 [pls/10min.] | AREA 1 [pls/10min.] | EACH AREA Σ [pls/10min.] |
|---|---|---|---|---|---|
| | | X3abc | X2abc | X1abc | X123abc |
| | | 1370 | 1610 | 1170 | 4150 |
| 400 | XNa | X3a | X2a | X1a | X123a |
| | ? | 86.3 | 201.4 | 719.2 | ? |

| | | X3bc =X3abc−X3a | X2bc =X2abc−X2a | X1bc =X1abc−X1a |
|---|---|---|---|---|
| | | 1283.7 | 1408.6 | 450.8 |
| 300 | XNb | X3b | X2b | X1b |
| | ? | ? | ? | ? |
| 200 | XNc | X3c | X2c | X1c |
| | ? | ? | ? | ? |

| SIZE [nm] | NUMBER CONCENTRATION [pls/ml] | AREA 3 [pls/10min.] | AREA 2 [pls/10min.] | AREA 1 [pls/10min.] | EACH AREA Σ [pls/10min.] |
|---|---|---|---|---|---|
| | | X3abc | X2abc | X1abc | X123abc |
| | | 1370 | 1610 | 1170 | 4150 |

| | X2c | X1c |
|---|---|---|
| | 400.6 | 100.1 |

| X2ab<br>=X2abc−X2c | X1ab<br>=X1abc−X1c |
|---|---|
| 1209.4 | 1069.9 |

| SIZE [nm] | NUMBER CONCENTRATION [pls/ml] | AREA 3 [pls/10min.] | AREA 2 [pls/10min.] | AREA 1 [pls/10min.] | EACH AREA Σ [pls/10min.] |
|---|---|---|---|---|---|
| | | X3abc | X2abc | X1abc | X123abc |
| | | 1370 | 1610 | 1170 | 4150 |
| 400 | XNa | X3a | X2a | X1a | X123a |
| | ? | 90 | 210 | 750.1 | ? |
| | | X3bc =X3abc−X3a | X2bc =X2abc−X2a | X1bc =X1abc−X1a | |
| | | 1280 | 1400 | 419.9 | |
| 300 | XNb | X3b | X2b | X1b | |
| | ? | ? | ? | ? | |
| 200 | XNc | X3c | X2c | X1c | |
| | ? | ? | ? | ? | |

| SIZE [nm] | NUMBER CONCENTRATION [pls/ml] | AREA 3 [pls/10min.] | AREA 2 [pls/10min.] | AREA 1 [pls/10min.] | EACH AREA Σ [pls/10min.] |
|---|---|---|---|---|---|
| | | X3abc | X2abc | X1abc | X123abc |
| | | 1370 | 1610 | 1170 | 4150 |
| 400 | XNa | X3a | X2a | X1a | X123a |
| | 300.0 | 90.0 | 210.0 | 750.1 | 1050.1 |
| 300 | XNb | X3b | X2b | X1b | X123b |
| | 800.0 | 280.0 | 1000.0 | 320 | 1600.0 |
| 200 | XNc | X3c | X2c | X1c | X123c |
| | 2500.0 | 1000.0 | 400 | 100 | 1500.0 |

FIG. 22

EVALUATION TEST OF LINEARITY FOR 200-nm PARTICLE REAGENT

| INPUT AMOUNT [pls/ml] | AVERAGE OF DISPLAY VALUE FOR 200nm [pls/ml] | AVERAGE OF DISPLAY VALUE FOR 300nm [pls/ml] | AVERAGE OF DISPLAY VALUE FOR 400nm [pls/ml] |
|---|---|---|---|
| 0 | 0.0 | 0.0 | 0.0 |
| 10 | 11.9 | 0.0 | 0.0 |
| 20 | 19.8 | 0.0 | 0.1 |
| 50 | 50.3 | 0.0 | 0.1 |
| 100 | 100.4 | 1.9 | 0.0 |
| 200 | 219.5 | 1.5 | 0.0 |
| 500 | 512.3 | 0.0 | 0.0 |
| 1000 | 1044.0 | 0.0 | 0.2 |
| 2000 | 2027.8 | 0.0 | 0.3 |
| 5000 | 4983.1 | 1.2 | 0.0 |
| 10000 | 10167.2 | 0.0 | 0.0 |

FIG. 24

| UNIT | NUMBER IN AREA 1 | NUMBER IN AREA 2 | NUMBER IN AREA 3 |
|---|---|---|---|
| 1 | A1 | B1 | C1 |
| 2 | A2 | B2 | C2 |
| 3 | A3 | B3 | C3 |
| ⋮ | ⋮ | ⋮ | ⋮ |
| 58 | A58 | B58 | C58 |
| 59 | A59 | B59 | C59 |
| 60 | A60 | B60 | C60 |

| $\Sigma$ | $\Sigma A1 \sim 60$ | $\Sigma B1 \sim 60$ | $\Sigma C1 \sim 60$ |
|---|---|---|---|

METHOD AND APPARATUS FOR DETECTING SIZE OF PARTICLES IN LIQUID

CROSS REFERENCE TO RELATED APPLICATIONS

This application is a Continuation of PCT International Application No. PCT/JP2008/002980 filed on Oct. 21, 2008, the entire contents of which is hereby incorporated by reference into the present application.

BACKGROUND ART

The present invention relates to a method and apparatus for monitoring a liquid for which the inclusion of impurities such as particles is disadvantageous, typified by ultrapure water that is, for example, used in semiconductor manufacturing, and for detecting the size of such particles.

In recent years, ultrapure water has become essential to wafer cleaning in semiconductor production processes. There are cases in which water includes impurities such as ions and colloidal particles, microbubbles and dissolved air, and particles (foreign particles) such as silica, cellulose acetate, and Teflon (registered trademark) polymer.

A measuring device that monitors the state of ultrapure water refined by a function membrane can be relatively easily realized by measuring conductivity with respect to ions. Also, in the case of air, since the active agent oxygen is the cause of defects, the measuring device can be realized by established technology for eliminating the actual influence of the air by removing all of the dissolved air with a degassing membrane, and thereafter reducing the partial pressure of oxygen by dissolving carbon dioxide that has been refined for static protection into the ultrapure water.

However, the technology that is farthest behind and has not caught up with the speed of progress in function membranes is an apparatus (particle sensor) for monitoring "foreign particles" in ultrapure water. In particular, it is no exaggeration to say that there is no product whatsoever that is suitable for inline constant monitoring for processes, and there is demand for a particle sensor that is easy-to-handle and inexpensive.

Various methods related to the detection of microparticles in water are known.

Specifically, there is a method of detecting the characteristics of microparticles included in a liquid by shining light into a specimen liquid and measuring the attenuation of the transmitted light or the amount of scattered light that has leaked laterally.

FIG. 26 is a diagram showing the configuration of a conventional scattered light-type detection apparatus 80.

As shown in FIG. 26, the scattered light-type detection apparatus 80 is composed of a laser light source 81, a lens 82 that converts light into parallel light, a transparent flow cell 83 that has rectangular cross section for allowing the flow of a reagent, and a light receiving element 84 that receives scattered light.

Light that has been emitted from the laser light source 81 is converted into parallel light by the lens 82, and incidences on the flow cell 83 while maintaining a uniform light intensity. If the light strikes a microparticle included in the reagent, scattered light is produced in an amount corresponding to the particle size of the microparticle, with a vector characterized by the particle size. The light receiving element 84 measures the intensity of the exiting scattered light and the angle relative to the flow cell 83, and the source microparticle size is determined from the obtained data.

With the scattered light-type method, due to the principle thereof, the vector of the exiting scattered light is a very important element. For this reason, if the flow cell 83 is given a round-tube shape, it will have the characteristics of a lens, and therefore the scattered light will be bent, and accurate measurement will not be possible. It is therefore necessary to use the rectangular cross section flow cell 83, which is very difficult to work, and this is a cause for a rise in cost and difficulty in maintenance.

Patent Document 1 discloses a detection method that does not have such shortcomings of the scattered light-type method. Specifically, Patent Document 1 discloses a method of focusing a light beam from a light source in a flow channel for a detection-target liquid, thus producing a radiant light beam, and then detecting, with use of a light detecting device, diffraction fringes that appear when particles pass by in the vicinity of the focal point. The time required for the particle to traverse the light beam is measured, and the dimensions of particles in the liquid are discriminated based on the relationship that the time from the appearance to the disappearance of diffraction fringes appearing due to particles passing by in the vicinity of the focal point is short, and the time from the appearance to the disappearance of diffraction fringes appearing due to particles passing by at positions away from the focal point is long, and also based on the relationship that the detectable passing position is limited according to the particle size of the particles. Accordingly, measuring the intensity and vector of light is not necessary as in conventional technology.

Patent Document 2 also discloses a method of measuring the particle size of microparticles. According to this method, a first measurement value that is correlated with the particle size of a microparticle included in a specimen fluid is detected from the output of at least one photoelectric conversion element, and a second measurement value that is correlated with a microparticle passing position is detected using a time difference between detections made by a pair of photoelectric conversion elements. Then, the first measurement value is corrected using the second measurement value, and the particle size of the microparticle is extracted.

However, in the case of using the method disclosed in Patent Document 1, there is a large constraint condition in actual use due to reasons particular to the principle of the method. When a reagent outside the constrain condition is measured, there is a problem with the accuracy of the display.

Specifically, the above method is effective when there is a sufficiently large number of particles included in the detection-target liquid, that is to say, in cases in which the detection target is tap water, lake water, or the like, but sufficiently precise detection is impossible for liquids in which the amount of particles contained is extremely small, such as ultrapure water. It should be noted that although tap water contains roughly several tens of thousands of microparticles per mL, ultrapure water used in wafer cleaning is said to contain microparticles on the order of 1/mL or less.

Since statistical processing is used in the method disclosed in Patent Document 1, it is impossible to ensure that the number of signals that are the basis of calculation is stochastically sufficient, and obtaining a stochastically significant number of signals requires too long of a measurement time and is not suitable for practical use. Also, since the calculation based on detected signals progresses in order from large particles to intermediate-size particles to small particles, a corresponding error accumulates.

Also, given that the method disclosed in Patent Document 2 corrects detected signal values that are correlated with particle sizes with use of detected passing position information, the characteristics of the detected signal values that in principle are correlated with particle sizes appear intensely, and therefore it is impossible to perform sufficient correction, and this method is not suited for the accurate detection of particle sizes. Moreover, Patent Document 2 does not disclose a correction method for accurately detecting particle sizes, and in view of this point as well, the accurate detection of particle sizes is impossible.

Patent Document 1: Japanese Patent No. 3745947
Patent Document 2: Japanese Patent No. 3301658

DISCLOSURE OF THE INVENTION

To address such problems, the present applicant previously proposed, as Japanese Patent Application No. 2007-172087, a method that can accurately detect particle sizes even when there are very few microparticles as impurities. According to this method, two light detection means are provided so as to be separated by a predetermined distance along the flow direction of a liquid, and for diffraction fringes detected by such light detection means, a peak time difference T2 that is a difference between times at which a detection level is maximal is measured, a passing time T1 that is a time from when the detection performed by one of the light detection means starts until when the detection performed by the other light detection means ends is measured, and the size of particles included in the liquid is detected based on the peak time differences T2 and passing times T1 that were measured.

In the case of using the previously proposed method, it was supposed that the relationship between the peak time difference T2 and the passing time T1 would be a curved line, but continued research performed thereafter found that the relationship between the time difference T2 and the passing time T1 is a group of points having a certain width between such curved line and the asymptote.

The present invention has been achieved on such finding, and an object thereof is to provide a method and apparatus for detecting the size of particles accurately and at low cost even when there are few microparticles as impurities included in a liquid.

A method according to the present invention is a method of detecting a size of particles in a liquid by irradiating a tube channel having translucency with coherent light such that the light traverses a flow direction of a liquid flowing in the tube channel, and detecting diffraction fringes that appear due to the particles by a light detection portion, a first light detection portion and a second light detection portion being provided as the light detection portion, and the second light detection portion being provided so as to be separated from the first light detection portion by a predetermined distance farther downstream along the flow direction of the liquid than the first light detection portion, and the method including the steps of: measuring, for each diffraction fringe detected in a predetermined time period by the first light detection portion and the second light detection portion, a peak time difference T2 that is a difference between times at which peak values appear in a detection signal from the first light detection portion and the second light detection portion, and an area SQ based on the waveform of the detection signal; and detecting a size of the particles included in the liquid based on the peak time differences T2 and the areas SQ that were measured.

Preferably, reference data is obtained in advance by performing actual measurement with use of a sample solution, and the reference data is recorded in a database, the reference data indicating, for a plurality of particle sizes, a relationship between each size and the peak time difference T2 and the area SQ that correspond to the size, wherein a size of the particles included in the liquid is detected with reference to the database.

Also, a plurality of areas for assignment of the diffraction fringes in accordance with the particle sizes may be defined in advance in a coordinate plane in which the peak time difference T2 is the x axis and the area SQ is the y axis; reference data may be obtained in advance by performing actual measurement with use of the sample solution, and the reference data may be recorded in the database, the reference data indicating, for the plurality of particle sizes, a relationship between each size and the number or proportion of diffraction fringes included in each of the plurality of areas; actual measurement data that indicates the number of diffraction fringes assigned to each of the plurality of areas based on the peak time differences T2 and the areas SQ that were measured may be acquired; and the number or proportion corresponding to each size of the particles included in the liquid may be detected with use of the reference data and the actual measurement data.

BRIEF DESCRIPTION OF THE DRAWINGS

FIG. 12 is a diagram showing the number of particles in each area for each size based on actual measurement data.

FIG. 15 is a diagram showing an example of reference data.

FIG. 16 is a diagram showing an example of measurement data.

FIG. 17 is a diagram showing calculation progression.
FIG. 18 is a diagram showing calculation progression.
FIG. 19 is a diagram showing calculation progression.
FIG. 20 is a diagram showing calculation progression.
FIG. 21 is a diagram showing calculation progression.
FIG. 22 is a diagram showing input amounts for a 200-nm particle reagent and the number of particles for each size obtained by measurement.

FIG. 24 is a diagram showing 60 units of accumulated measurement data.

BEST MODE FOR CARRYING OUT THE INVENTION

According to the embodiment described below, it is possible to detect the size of particles accurately and at low cost even when there are few microparticles as impurities included in a liquid.

Overview of Configuration of Detection Apparatus 1

Figure 1:
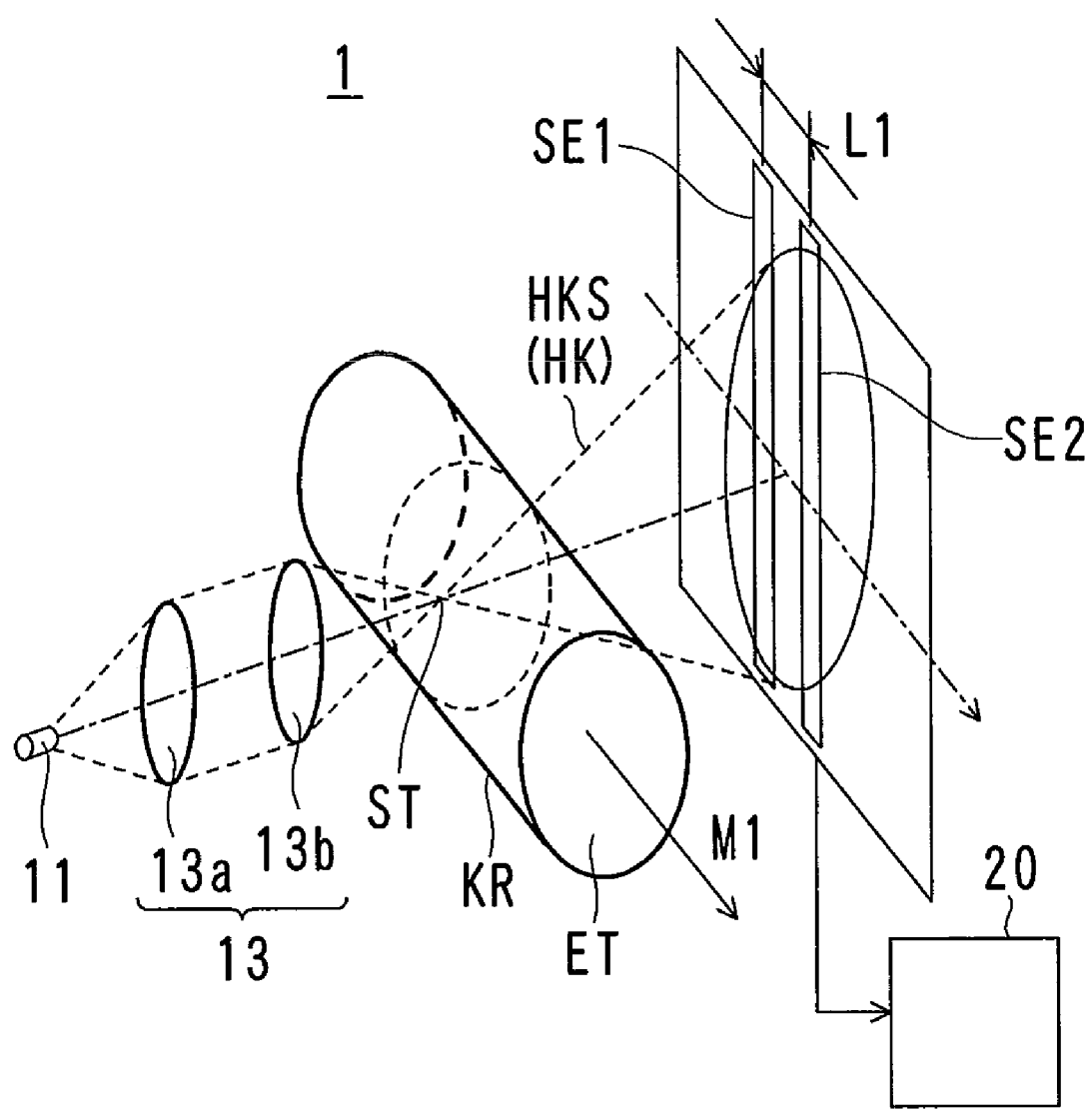
FIG. 1 is a perspective view showing a detection apparatus according to an embodiment of the present invention.
Figure 2:
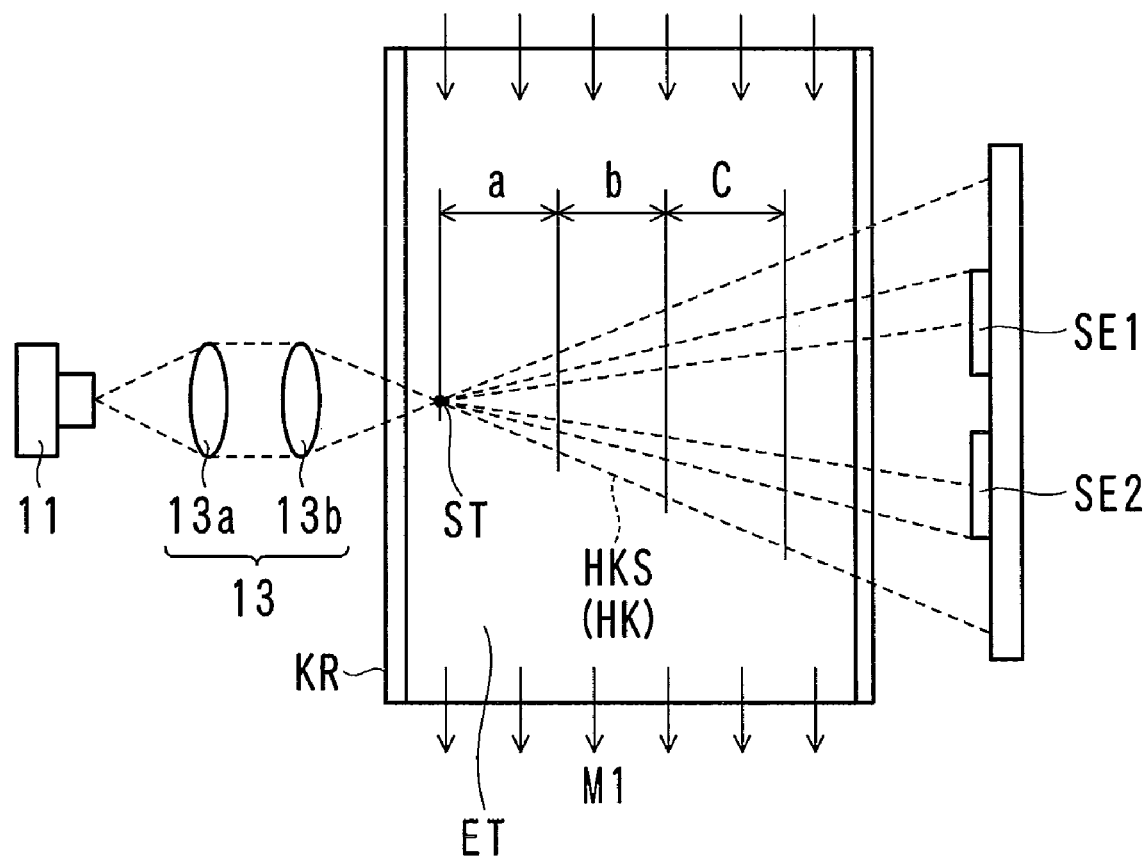
FIG. 2 is a diagram showing the detection apparatus as viewed planarly.

As shown in FIGS. 1 and 2, in a detection apparatus 1, the size of particles (particle size) is detected by irradiating a tube channel KR having translucency with coherent light HK such that the light HK traverses the tube channel KR orthogonally relative to a flow direction M1 of a flowing liquid ET, and detecting, with use of a light detection means SE, diffraction fringes AM that appear due to particles included in the liquid ET.

A laser light source 11 and a lens 13 are used to generate the coherent light HK. Although various devices can be used as the laser light source 11, diffraction fringes more readily appear when the output is as high as possible and the wavelength is as short as possible. Combinations of different ones of various types of lenses may be used as the lens 13.

Note that as the laser light source 11, it is possible to use a device that has, for example, a laser wavelength of 405 nm and a laser output of 35 mW, or another device. As the flow cell, it is possible to employ a flow cell having an arbitrary shape as long as it is translucent. For example, it is possible to use a flow cell manufactured using fused silica glass and having an inner diameter of 10 mm, or the like. As the light detection means SE, it is possible to use a light receiving element such as a photodiode or a phototransistor, or an image pickup device such as a CCD. In the case of using an image pickup device, it is sufficient to use two areas in one image pickup device as first and second light detection means SE1 and SE2, each area being composed of pixels or pixel groups that are separated at an appropriate distance.

Figure 4:
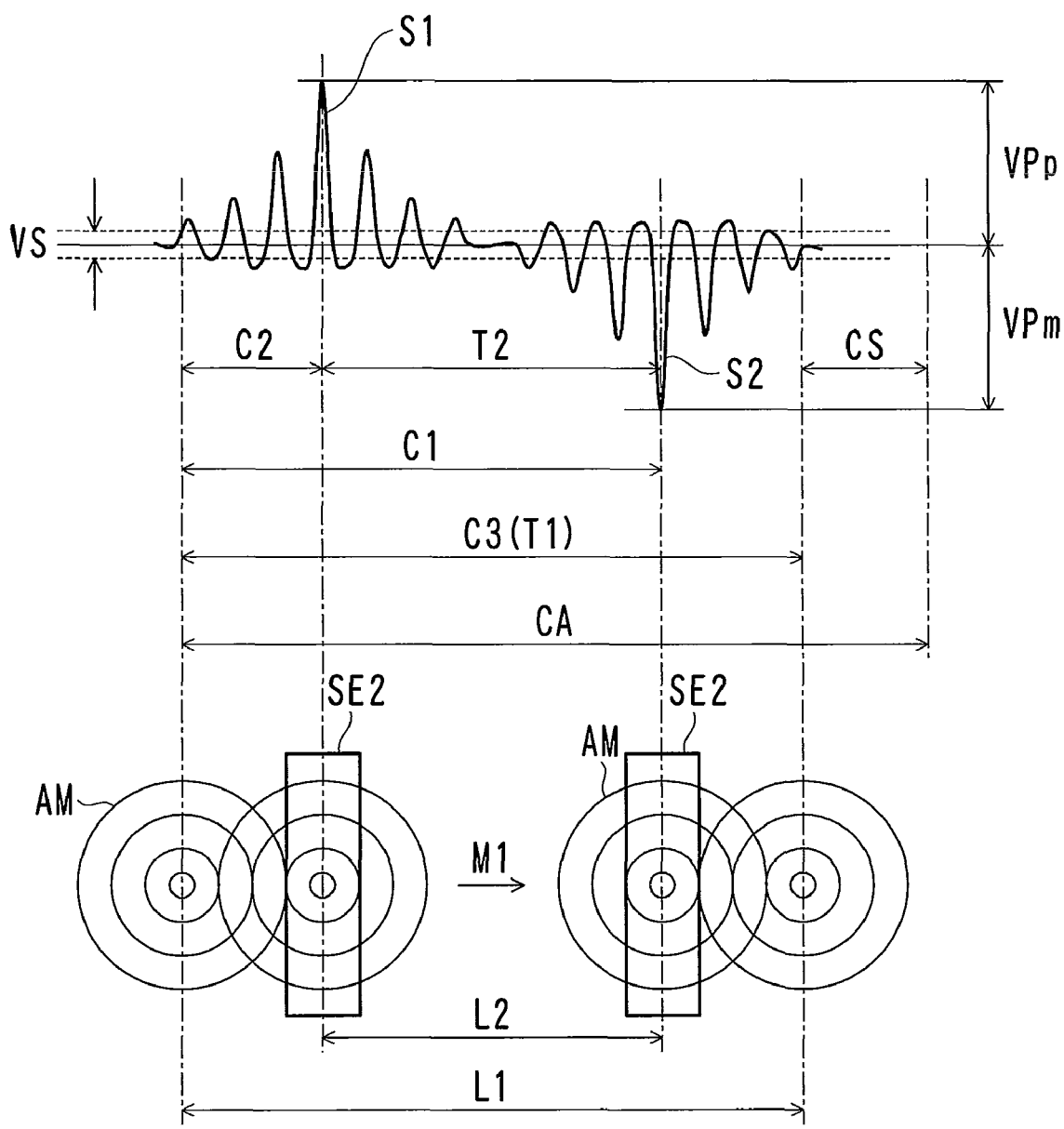
FIG. 4 is a diagram showing the state of a detection signal based on diffraction fringes.
Figure 5:
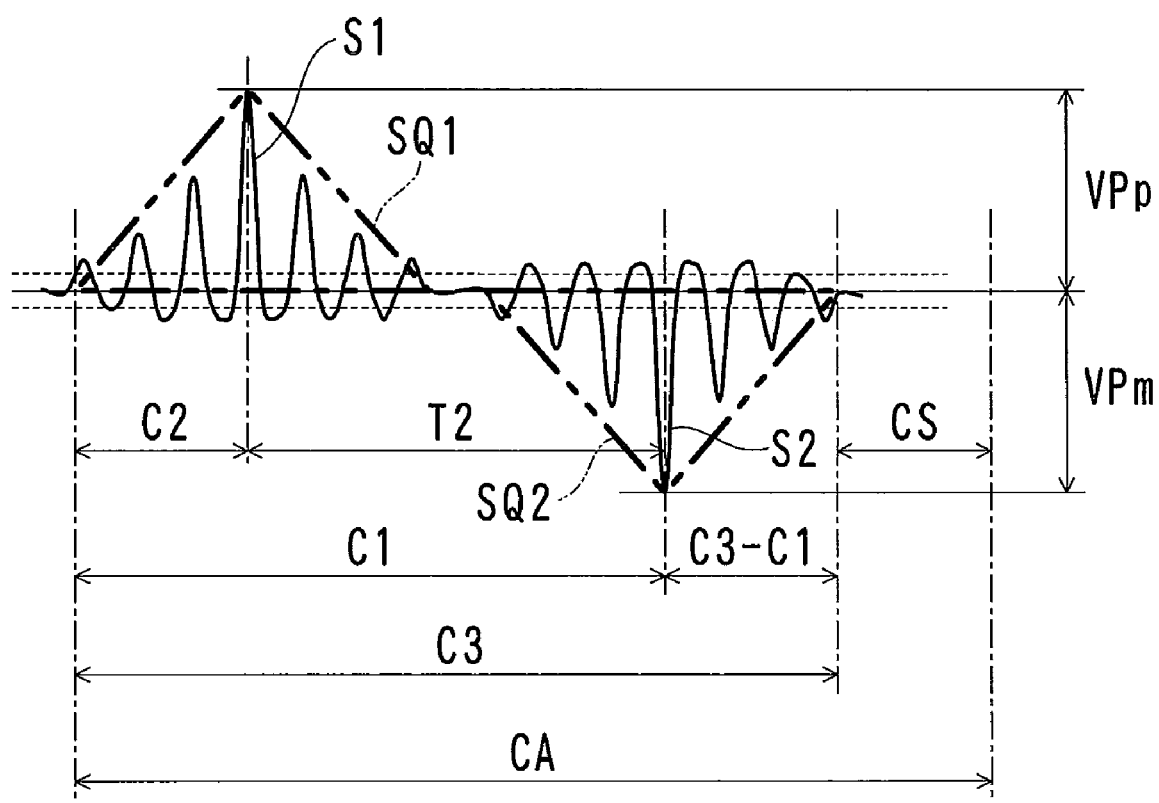
FIG. 5 is a diagram for describing a method of obtaining an area SQ based on the waveform of the detection signal.

As shown in FIGS. 4 and 5, the first light detection means SE1 and the second light detection means SE2 are provided as the light detection means SE. The second light detection means SE2 is provided so as to be separated from the first light detection means SE1 by a predetermined distance L2 farther downstream along the flow direction M1 of the liquid ET than the first light detection means SE1.

Also, the first light detection means SE1 and the second light detection means SE2 are disposed so as to receive, among the range in which the radiant light is projected, the entire range in the right angle direction relative to the flow direction of the liquid ET at the position of the respective light detection means SE1 and SE2.

For the diffraction fringes AM detected by the first and second light detection means SE1 and SE2, detection signals (output signals) S1 and S2 are acquired from the first light detection means SE1 and the second light detection means SE2.

Then, a peak time difference T2 that is a difference between times at which the peak values of the detection signals S1 and S2 appear is measured, and an area SQ based on the waveforms of the detection signals S1 and S2 is measured. The size of particles included in the liquid ET is detected based on the peak time differences T2 and areas SQ that have been measured.

Also, for multiple sizes of particles, reference data indicating a relationship between each size and a corresponding peak time difference T2 and area SQ is obtained in advance by performing actual measuring using a test solution and recorded in a database DB1, and the size of particles included in the liquid ET is detected with reference to the database DB1.

Also, multiple areas for assigning diffraction fringes according to particle size are defined in advance in a coordinate plane in which the peak time difference T2 is the x axis and the area SQ is the y axis, and for multiple sizes of particles, reference data indicating a relationship between each size and a number or proportion of diffraction fringes included in the respective areas is obtained in advance by performing actual measuring using a test solution and recorded in a database, actual measurement data indicating the number of diffraction fringes assigned to the respective areas is acquired based on the measured peak time differences T2 and areas SQ, and the particle number or proportion corresponding to each size of particle included in the liquid ET is detected with use of the reference data and the actual measurement data.

Also, the number corresponding to each size of the particles included in the liquid ET is detected by dividing the numbers of diffraction fringes indicated in the actual measurement data among the areas for each size by performing a simulation with reference to the reference data.

Note that the area SQ is obtained by approximation with a triangle whose base is the duration of the waveforms of the detection signals S1 and S2 and whose height is the crest value of the waveforms.

The following is a more detailed description.

Detection of Diffraction Fringes AM

In the detection apparatus 1, radiating light HKS (radiant light) whose focal point ST is in the liquid ET is used as the light HK. The database DB1 shown in FIG. 3 has recorded therein data indicating a relationship between the peak time difference T2 and the area SQ for multiple particle sizes. This data is reference data DK that is described later. Also, the database DB1 may have recorded therein various arithmetic expressions used for obtaining particle sizes from peak time differences T2 and areas SQ that have been measured.

In FIG. 2, the light (laser light) that irradiates from the laser light source 11 through the lens 13 onto the liquid ET is the radiant light HKS whose focal point is in the liquid ET. Accordingly, the farther away a particle is separated from the focal point ST, the longer the distance the particle travels to traverse the radiant light HKS. Here, since the particles are dispersed uniformly in the liquid ET that is flowing at a constant flow speed, the passing speed of the particles is also constant, and as a result, the time required for a particle to traverse the radiant light HKS increases proportionately to the distance from the focal point ST.

If this is viewed in terms of diffraction fringes AM appearing due to the particles, the time required for the process in which a diffraction fringe AM appears, moves, and disappears as the diffraction fringe AM traverses the light receiving face of the light detection means SE is shorter for a diffraction fringe AM that appears due to a particle passing in the vicinity of the focal point ST, and therefore the moving speed of the diffraction fringe AM is fast, and the width (duration) of the output signals S1 and S2 from the light detection means SE is short. Conversely, a diffraction fringe AM appearing due to a particle far away from the focal point ST takes a long time to traverse the light receiving face, and therefore the moving speed of the diffraction fringe AM is slow, and the width of the output signals S1 and S2 from the light detection means SE is long.

Meanwhile, the radiant light HKS whose focal point ST is in the liquid ET has the characteristic that as the passing position is closer to the focal point ST, even smaller-sized particles cause diffraction fringes to appear. In other words, a small particle cannot cause a diffraction fringe to appear unless the particle passes at a position close to the focal point ST. In contrast, a large particle causes a diffraction fringe AM to appear even if the particle has passed far away from the focal point ST, and therefore such a particle can be detected.

When this is combined with the above-described physical phenomenon related to diffraction fringes, only large particles can be detected easily with use of merely signals, namely the output signals S1 and S2. The problem is signals based on diffraction fringes AM appearing due to particles in the portion of the range indicated by "a" of FIG. 2, and since there is no method for directly distinguishing such diffraction fringes based on merely signals, the above-described method disclosed in Patent Document 1 introduced the thinking based on statistical processing.

In the present embodiment, as a technique for finding out what size of particle caused the generation of an obtained merely signal, as shown in FIG. 2, the two light detection means SE1 and SE2 are used, and they are disposed parallel in the flow direction M1 of the liquid ET.

A diffraction fringe AM appears when the highly coherent radiant light HKS is disturbed by a microparticle, with the microparticle itself as the singularity, and the diffraction fringe AM is a concentric fringe pattern. The central part of a diffraction fringe AM is as if light were focused by a lens, and has the highest light intensity. Accordingly, in the case of measuring a diffraction fringe AM with the light detection means SE, it is possible to observe a clear peak value. At the moment when the peak value is observed, the central part of the diffraction fringe AM is overlapped with the center of the light detection means SE.

By using the two light detection means SE1 and SE2, it is possible to easily find out, by peak-to-peak, the time required for the center point of the diffraction fringe AM to pass the distance L2 between the two light detection means SE1 and SE2. This peak-to-peak passing time is the time from one appearance to another appearance of the center point of the diffraction fringe AM, and therefore regardless of the distance from the central portion to the peripheral portion of the diffraction fringe AM, that is to say, the size of the diffraction fringe AM, this time is uniquely determined by the position at which a microparticle traverses the radiant light HKS and the distance to the focal point ST. In other words, if two different signals are observed and the times T2 thereof are the same, the passing positions of the microparticles on which the signals are based are the same distance from the focal point ST.

On the other hand, if microparticles pass at positions that are the same distance from the focal point ST, the light density at the positions is the same, and therefore it is the size of the passing microparticles that is the constituent that determines the size (diameter) of the diffraction fringes AM observed at the light receiving faces of the light detection means SE. The microparticles are subjected to the same light density since they are the same distance from the focal point ST, and the scattered light from the microparticles is proportional to the surface area of the microparticles, and as a result, a diffraction fringe AM having a larger diameter appears due to a larger particle. T1 is the time from when a diffraction fringe AM appears in the light path of the radiant light HKS and strikes the light detection means SE1 until when the diffraction fringe AM has completely passed the light detection means SE2. The time T1 includes a quantity obtained by converting a distance corresponding to the diameter of the diffraction fringe AM into a time.

With the previously described Japanese Patent Application No. 2007-172087, T1 is the time (passing time) from when a diffraction fringe AM strikes the light detection means SE1 until the diffraction fringe AM has completely passed the light detection means SE2, T2 is the time (peak time difference) obtained by peak-to-peak, and particle sizes are obtained based on T1 and T2. In other words, in the exemplary case in which the particle sizes are 0.1 µm, 0.2 µm, and 0.3 µm, the relationship between the peak time difference T2 and the passing time T1 is as indicated by virtual curved lines CV4 to CV6 in FIG. 6. These virtual curved lines CV4 to CV6 are the result of performing a simulation with a convergence-type monitor.

Since this simulation is based on convergence, the closer to the position of the focal point ST in the tube channel KR, the higher the intensity of laser light that particles are subjected to, and furthermore the faster the moving speed of the diffraction fringe AM. The distance from the focal point ST appears as the peak time difference T2, and if peak time differences T2 for two particles are the same, such particles passed at the same distance from the focal point.

Figure 6:
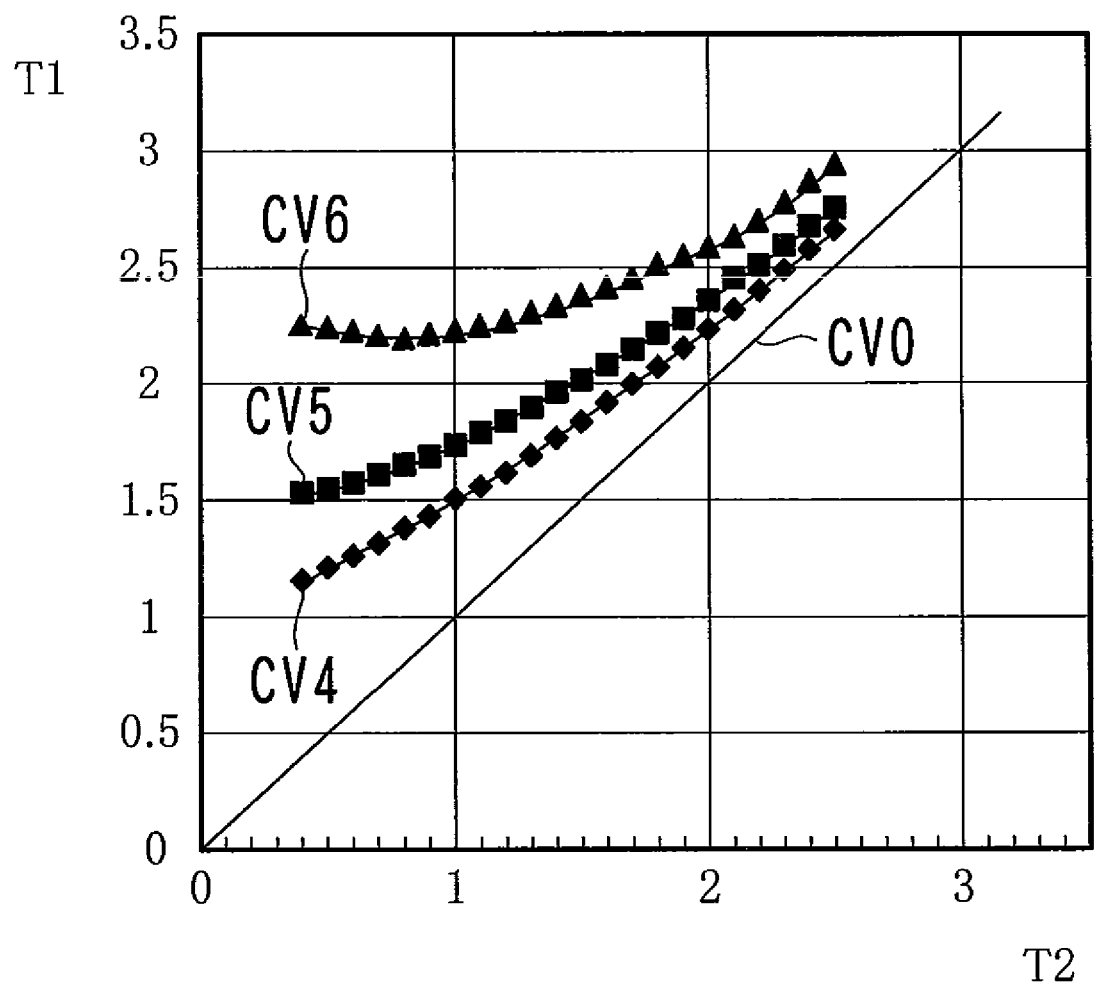
FIG. 6 is a diagram showing a relationship between particle size, passing time T1, and peak time difference T2 as predicted by a simulation.
Figure 7:
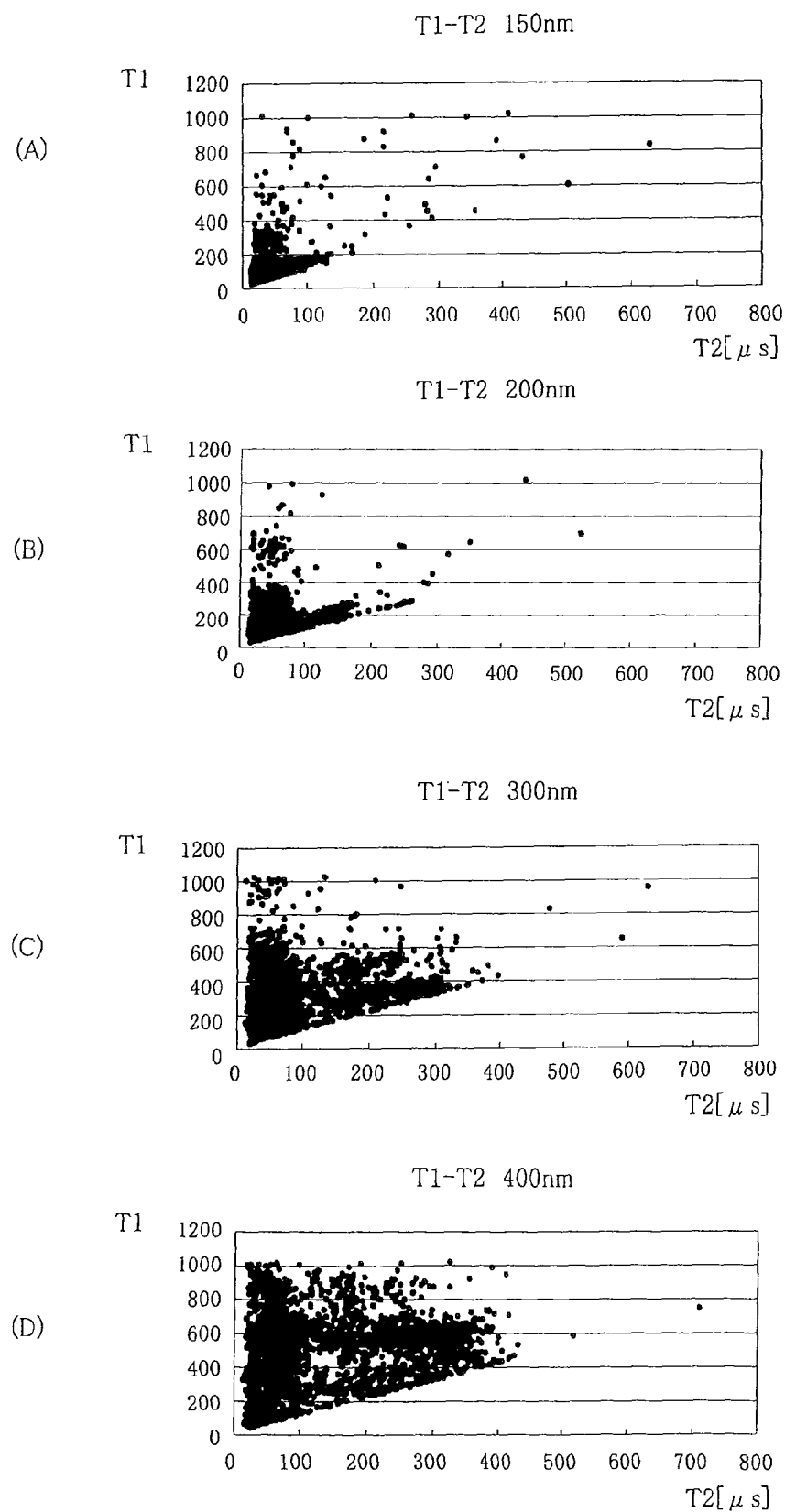
FIGS. 7(A) to 7(D) are diagrams showing relationships between particle size, passing time T1, and peak time difference T2 as obtained by experimentation.
Figure 8:
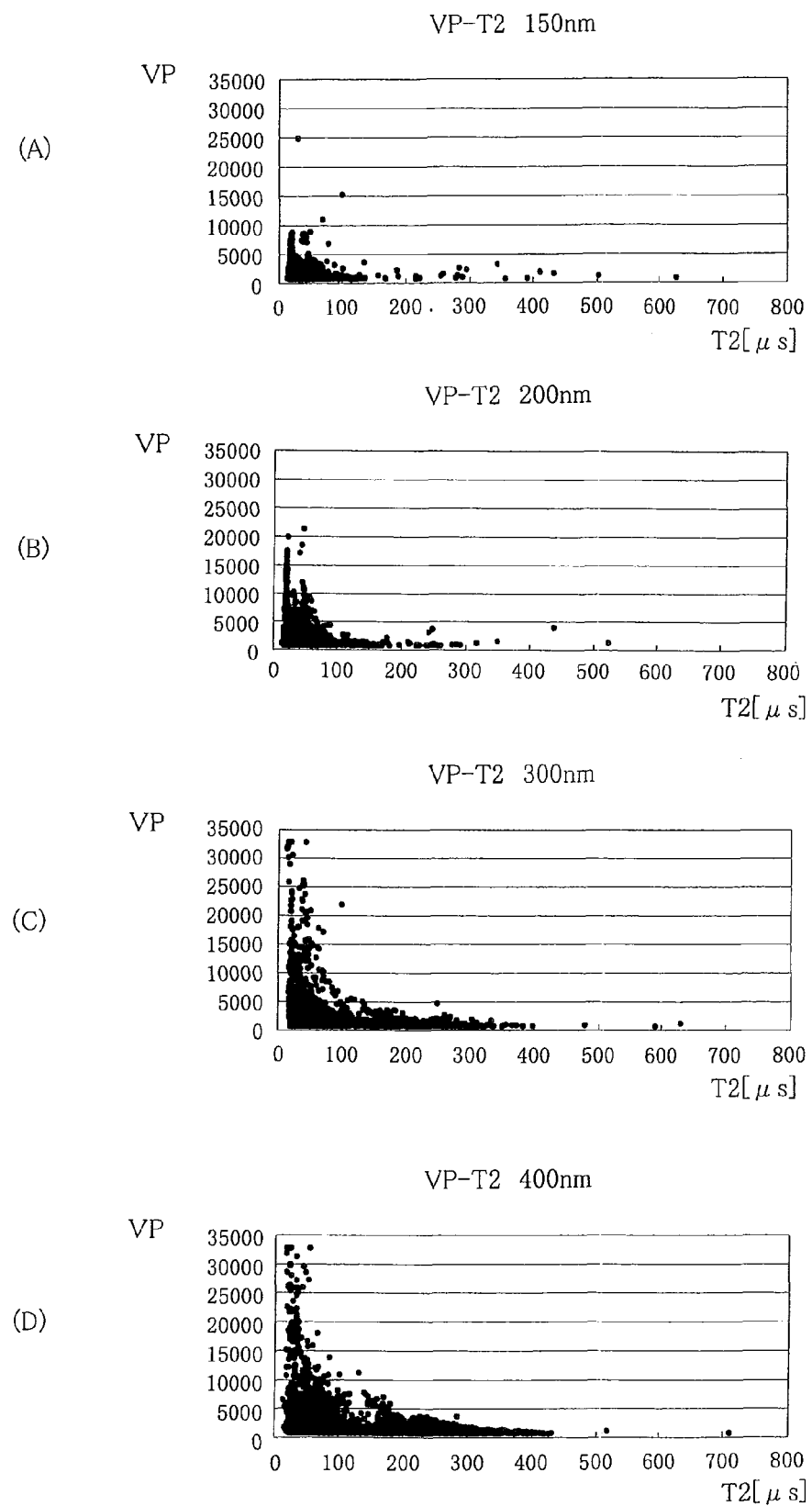
FIGS. 8(A) to 8(D) are diagrams showing relationships between particle size, peak time difference T2, and waveform peak value as obtained by experimentation.
Figure 9:
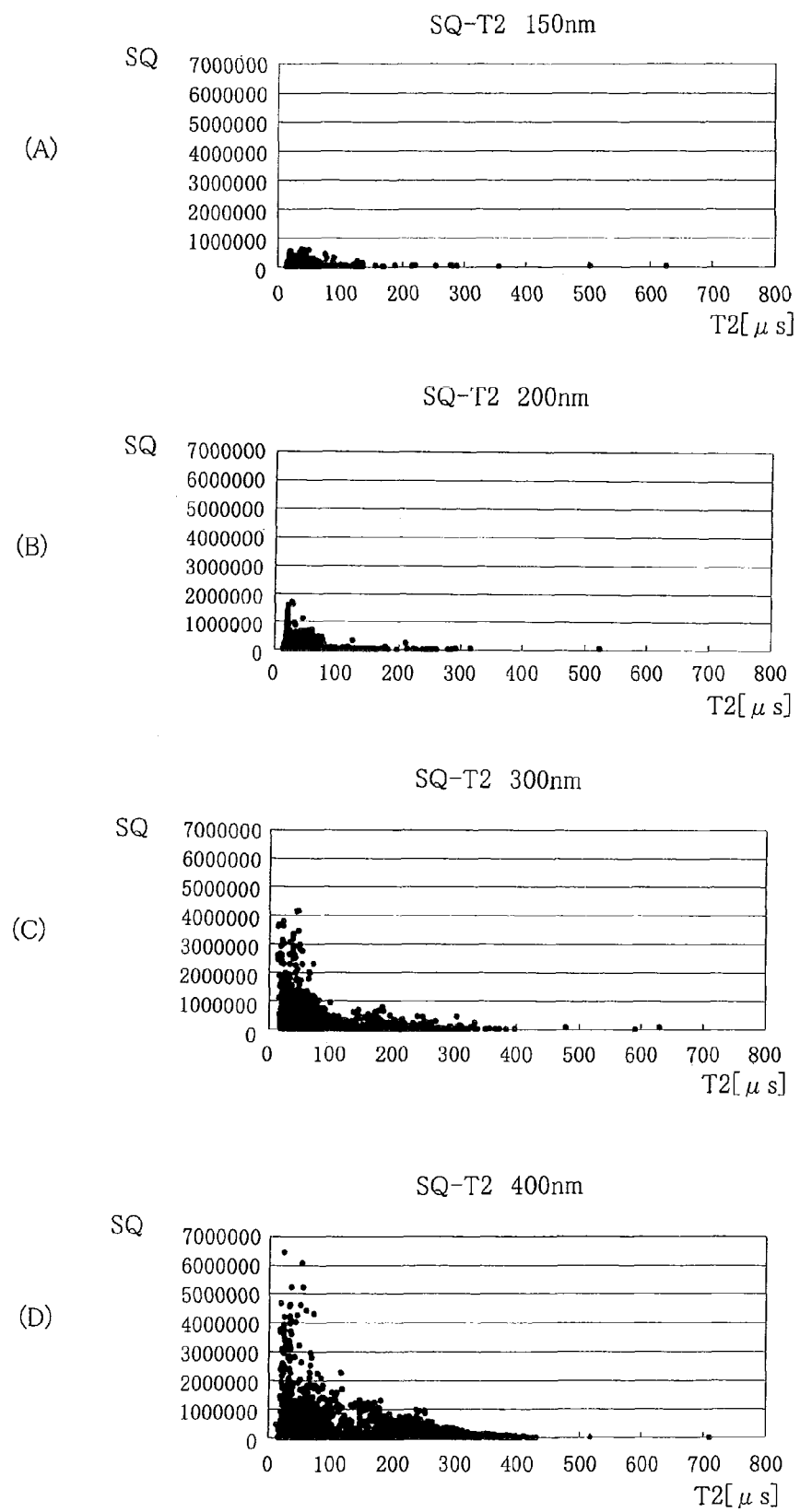
FIGS. 9(A) to 9(D) are diagrams showing relationships between particle size, peak time difference T2, and area SQ as obtained by experimentation.

Accordingly, as shown in FIG. 6, particles have been subjected to the same intensity of laser light if the peak time differences T2 are the same, and therefore when particles are small, the diffraction fringes AM are also small, and the peak time differences T2 and passing times T1 head in the direction of becoming the same. Also, since the passing position of particles is farther from the focal point ST if the peak time difference T2 is higher, the intensity of laser light that the particles are subjected to attenuates so as to be inversely proportional to the square of the distance, and therefore the diffraction fringes AM are also accordingly smaller, and the peak time differences T2 and the passing times T1 head in the direction of becoming the same. Accordingly, the curved lines CV4 to CV6 converge with a straight line CV0 indicating T1=T2, as the asymptote.

Distribution Based on Actual Measurement Data DJ

However, although the simulation yields the results shown in FIG. 6, the actual results are different since there are differences in various detailed conditions.

Specifically, FIGS. 7(A) to 7(D) show the results of performing an experiment with four types of reagents that respectively have particle sizes of 0.15 µm, 0.20 µm, 0.30 µm, and 0.40 µm, and actually measuring the relationship between the peak time difference T2 and the passing time T1 for each. Each detected particle is shown by a black dot on a coordinate plane in which the peak time difference T2 is the x axis and the passing time T1 is the y axis.

In this experiment, for each size, approximately 3,000 particles were detected by measuring for 10 minutes (see FIG. 12). Not only were the peak time difference T2 and the passing time T1 measured for the diffraction fringe AM for each particle, but also times C1 to C3 and peak values VPp and VPm of the waveforms and the like shown in FIG. 4 were measured, and such actual measurement data DJ was recorded in a memory.

Note that as shown in FIG. 4, the output signal S2 of the second light detection means SE2 is inverted and composited with the output signal S1 of the first light detection means SE1. The reason for this is that by removing the direct current component from the output signals S1 and S2, the state in which no diffraction fringe AM exists, that is to say, the state in which no waveform exists is set to 0 volts, and the waveforms are indicated with 0 volts being the reference. The compositing of such signals can be easily realized with use of, for example, an addition circuit, a subtraction circuit, or a differential amplifier circuit in which an operation amplifier is used.

In this experiment, parameters VS, CS, and CA shown in FIG. 4 were set as shown below.

VS: threshold that determines the start and stop of time measurement

CS: count value of duration for which waveform continues to exceed the threshold value VS (for stop determination)

CA: count value from when waveform exceeds threshold value VS until ceases to exceed the threshold value VS Specifically, a not-shown time measurement counter for measuring time when the waveforms of the output signals S1 and S2 based on a diffraction fringe AM have exceeded the threshold value VS is started, and the time measurement counter is stopped when the threshold value VS is no longer exceeded. The count value of the time measurement counter therefore shows a time.

The time measurement counter is forcibly stopped when CA has exceeded a pre-set maximum value. Also, when CA is less than a pre-set minimum value, such data is not considered to be related to a diffraction fringe AM appearing due to a particle, and such data is discarded.

Also, the measurement values are indicated as shown below.

VPp: positive peak value of waveform (15-bit)
VPm: negative peak value of waveform (15-bit)
C1: count value from start until peak value VPm
C2: count value from start until peak value VPp
C3: count value for entire length of waveform (CA-CS)

As shown in FIGS. 7(A) to 7(D), the dots indicating particles are not aligned linearly, but instead are scattered in a group having a spread. Moreover, it can be seen that the dots are concentrated between curved lines corresponding to the above-described curved lines CV4 to CV6 and the straight line CV0 that is the asymptote. However, it can be seen that there are also many scattered dots separated from the concentrated group of dots.

In view of this, FIGS. 8(A) to 8(D) show the relationship between the peak time difference T2 and the peak value VP for each particle based on the actual measurement data DJ.

As shown in FIGS. 8(A) to 8(D), the dots indicating particles are concentrated in the vicinity of the coordinate origin and form a group. It appears that the dots are concentrated between the x axis, the y axis, and a virtual curved line that appears to be a hyperbolic line. It can also be seen that as the size of the particle increases, the virtual curved line moves in a direction of separation from the coordinate origin.

However, it can be seen that even in this case, there is still also a large number of scattered dots separated from the concentrated group of dots.

In view of this, instead of the relationship between the peak time difference T2 and the peak value VP, the relationship between the peak time difference T2 and the area SQ based on the waveforms of the detection signals S1 and S2 is furthermore shown in FIGS. 9(A) to 9(D). Here, the area SQ of the waveforms is indicated by the following expression (1).

$$SQ = VPp \times C2 + VPm \times (C3-C1) \quad (1)$$

In other words, as shown in FIG. 5, the area SQ is obtained by approximating the sum of the areas of two triangles whose bases are the durations of the waveforms of the output signals S1 and S2 [$C2 \times 2$, $(C3-C1) \times 2$], and whose heights are respectively the peak values VPp and VPm.

In FIGS. 9(A) to 9(D), the dots indicating the particles are further concentrated in the vicinity of the coordinate origin and form a group. It appears that the dots are concentrated between the x axis, the y axis, and a virtual curved line that appears to be a hyperbolic line. It can also be seen that as the size of the particle increases, the virtual curved line moves in a direction of separation from the coordinate origin.

However, in FIGS. 9(A) to 9(D), the number of scattered dots that are separated from the group of dots is less than in the cases shown in FIGS. 8(A) to 8(D).

In this way, in the case of showing dots indicating particles on a coordinate plane, by using the area SQ based on the waveforms of the detection signals S1 and S2 as the parameter instead of the peak value VP, there is less scattering in the distribution of particles, and there is a high degree of correlation between the two parameters, that is to say, the peak time difference T2 and the area SQ.

In other words, the peak value VP of the waveforms of the output signals S1 and S2 reflect the contrast of the luminance of the diffraction fringes AM. As the particle size increases, there is an increase in the length of the base of the triangles and their height. By using both of these, it is possible to cause the scattered dots to converge, and perform accurate assigning to each size.

In this way, by using the two-dimensional area SQ instead of the one-dimensional peak value VP as the parameter for determining the correlation with particle size, the scattering in the distribution of dots indicating particles is thereby absorbed, and a distribution with an even higher degree of correlation is obtained. Since particle sizes are detected based on such a distribution, the particle sizes are detected accurately.

The following is a description of an example of a specific method for detecting particle sizes based on the peak time difference T2 and the area SQ.

Assignment of Particles to Areas HR

As can be seen in a comparison among FIGS. 9(A) to 9(D), approximately 3,000 particles whose size is 0.15 µm are concentrated in a small area, and for the same number of particles, the area widens as the particle size increases to 0.20 µm, 0.30 µm, and 0.40 µm.

The inventors of the present invention focused on this point, and based on the change in the areas in the distributions due to the difference in size, gave thought to defining multiple areas to which dots are assigned in accordance with particle sizes.

Specifically, as the areas corresponding to particle sizes, the coordinate plane is partitioned into a first area, a second area, and a third area, beginning from a position close to the coordinate origin.

Figure 10:
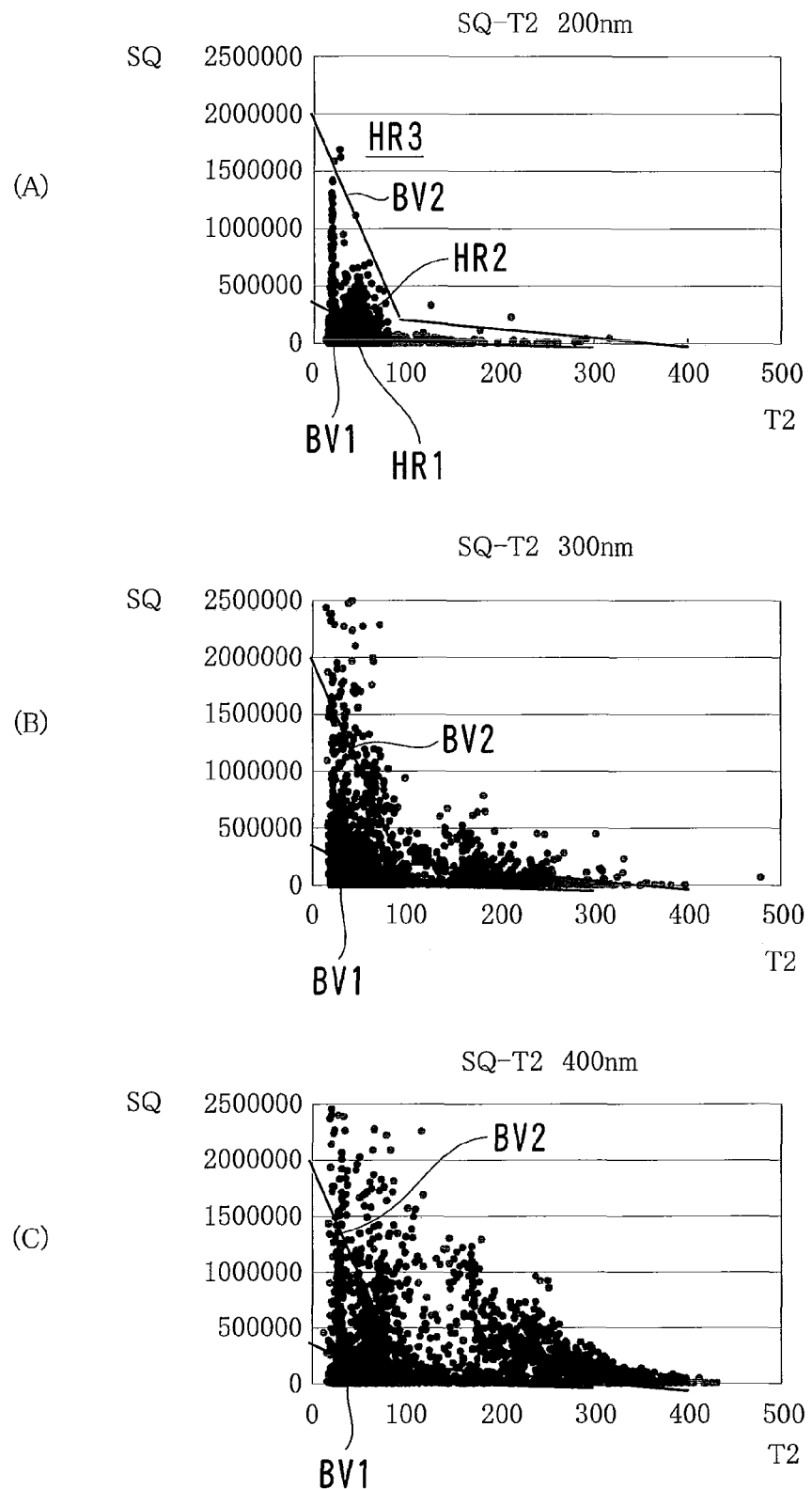
FIGS. 10(A) to 10(C) are diagrams showing areas on SQ-T2 coordinate planes.

In FIGS. 10(A) to 10(C), three areas HR1 to HR3 are partitioned using two curved lines BV1 and BV2 as their boundaries. Note that FIGS. 10(A) to 10(C) show cases in which the particle sizes were 0.20 µm, 0.30 µm, and 0.40 µm in correspondence with FIGS. 9(B) to 9(D).

Figure 11:
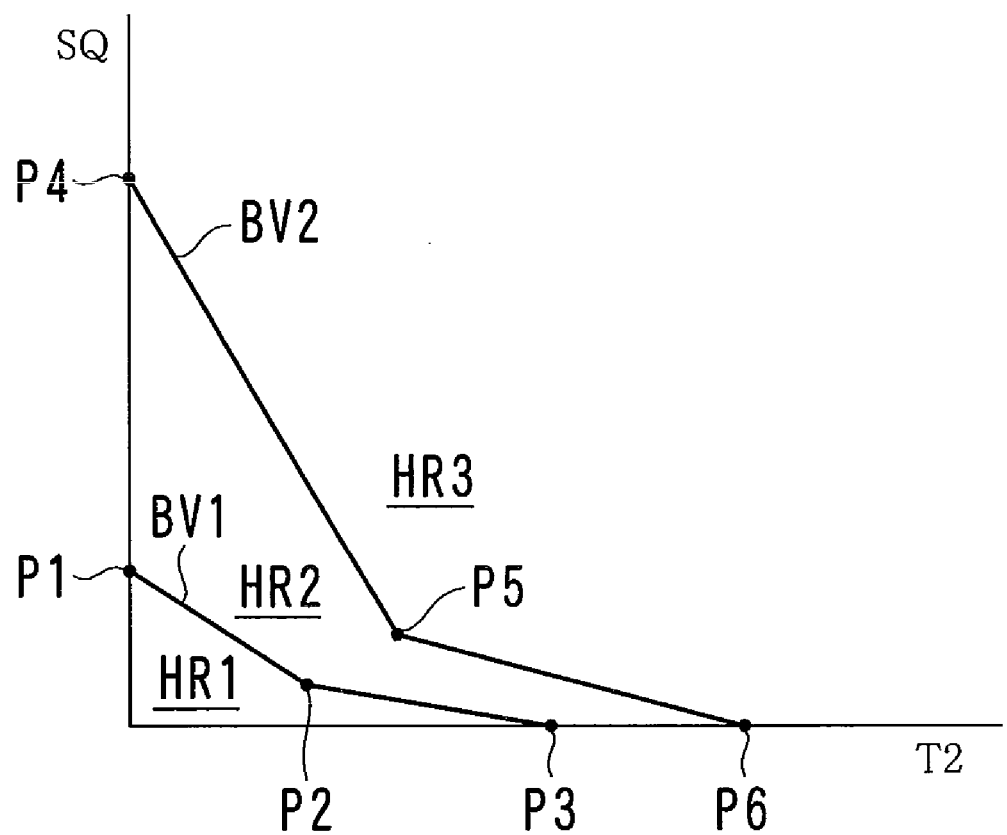
FIG. 11 is a diagram for describing an area and its boundary lines.

Specifically, in the present embodiment, as shown in FIG. 11, the curved line BV1 is composed of two straight lines that connect three points P1 (0, 400000), P2 (80, 25000), and P3 (300, 0), and the curved line BV2 is composed of two straight lines that connect three points P4 (0, 2000000), P5 (90, 250000), and P6 (400, 0).

In FIG. 11, the area HR1 is the range bounded by the x axis, the y axis, and the curved line BV1, the area HR2 is the range bounded by the curved line BV1, the curved line BV2, the x axis, and the y axis, and the area HR3 is the range outward of the curved line BV2. Note that "area HR1", "area HR2", and "area HR3" are sometimes indicated as "area 1", "area 2", and "area 3" respectively.

Note that as can be seen in FIGS. 10(A) to 10(C), many of the dots indicating the particles whose size is 0.20 μm are inside the area HR1, and a large number of dots are also inside the area HR2. Many of the dots indicating the particles whose size is 0.30 μm are inside the area HR1 and the area HR2, and a large number of dots are also inside the area HR3. The dots indicating the particles whose size is 0.40 μm are scattered in the areas HR1, HR2, and HR3. Almost all of the dots indicating the particles whose size is 0.15 μm are expected to be inside the area HR1.

Generation of Reference Data DK

Figure 13:
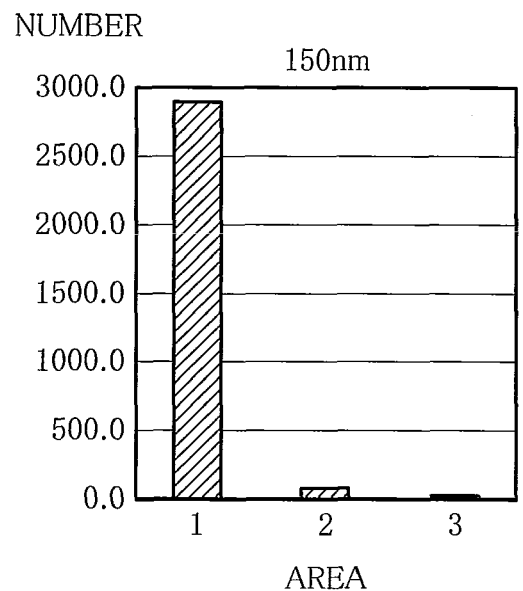
FIGS. 13(A) to 13(D) are diagrams in which the number of particles in each area for each size based on actual measurement data is shown by graphs.
Figure 13:
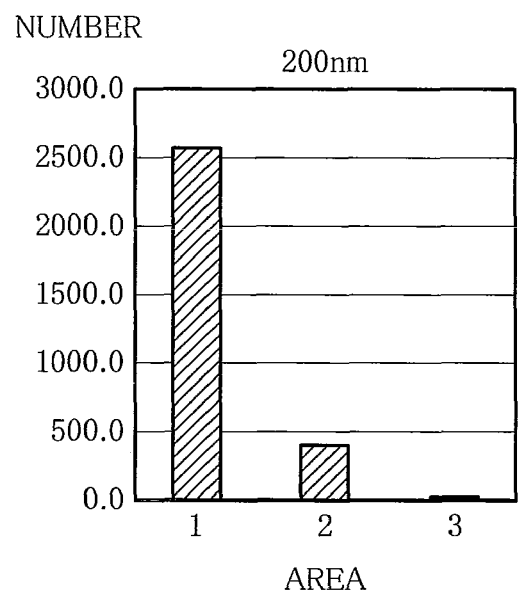
Figure 13:
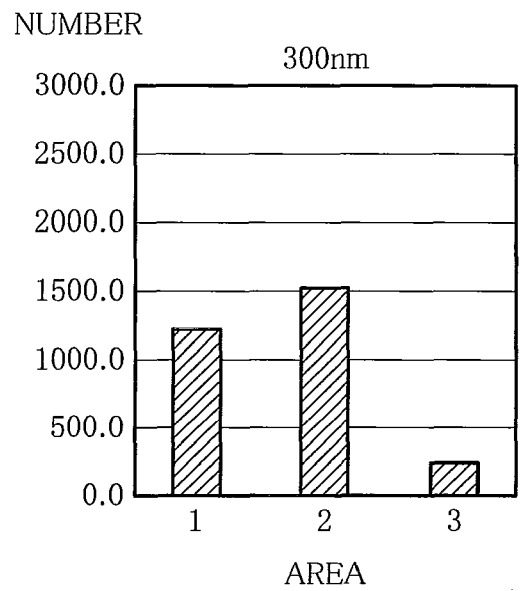
Figure 13:
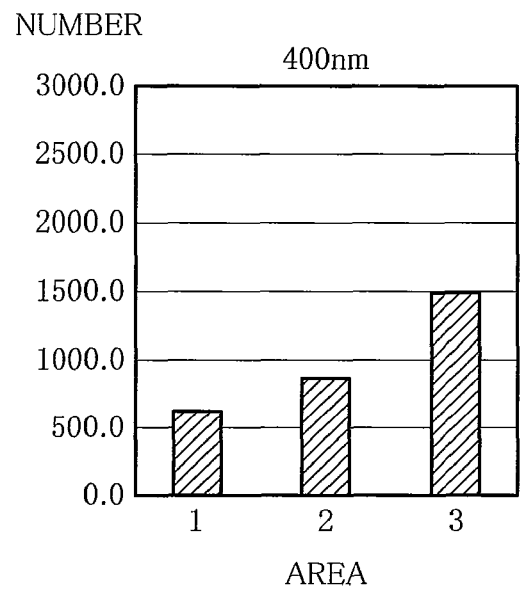

Meanwhile, FIGS. 12 and 13 show part of the actual measurement data DJ obtained using the above-described reagents, and the number of particles assigned to the areas HR1 to HR3 based on the actual measurement data DJ.

Specifically, as shown in FIG. 12, approximately 3,000 particles were detected by performing 10 minutes measurement for each reagent including a different size of particles. The particles were assigned to the areas HR1 to HR3 as shown in FIGS. 12 and 13, in accordance with the areas SQ and peak time differences T2 indicated in the actual measurement data DJ.

Next, consider the ratio of the number of particles assigned to the areas HR1 to HR3 for each size, that is to say, the ratio (area ratio) between the number N1 in the area HR1, the number N2 in the area HR2, and the number N3 in the area HR3. As can be seen in FIGS. 12 and 13, N1:N2:N3 is approximately 31:1:0 for the particles whose size is 0.15 μm, approximately 13:2:0 for the 0.20 μm particles, approximately 5:6:1 for the 0.30 μm particles, and approximately 3:5:7 for the 0.40 μm particles.

In the present embodiment, the reference data DK is obtained that is data indicating a correlation between each particle size and such distributions of numbers according to particle sizes, that is to say, the number of dots whose coordinates are determined by the area SQ and the peak time difference T2 that are inside the areas HR1 to HR3, the proportion of such dots that are inside the areas HR1 to HR3, or the like. Then, for a liquid ET for which the size of particles included therein is unknown, the size of such particles is detected based on the reference data DK.

In other words, in the present embodiment, instead of obtaining particle sizes by correction, the size of particles is directly established by a so-called area distribution method in which particle sizes are obtained by distribution to the areas HR1 to HR3 in accordance with the areas SQ and the peak time differences T2.

Figure 14:
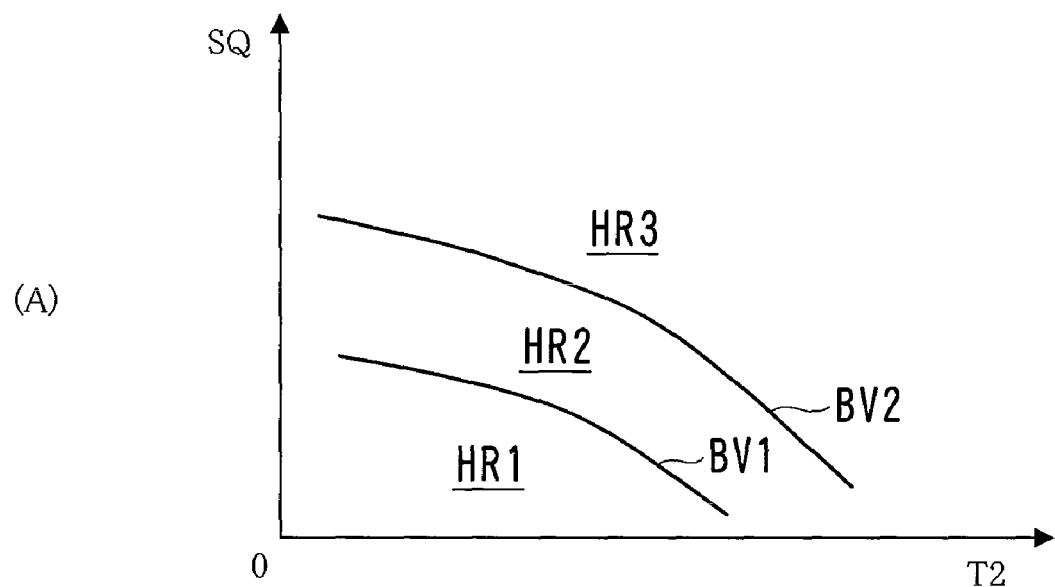
FIGS. 14(A) and 14(B) are diagrams showing examples of other ways of defining areas.
Figure 14:
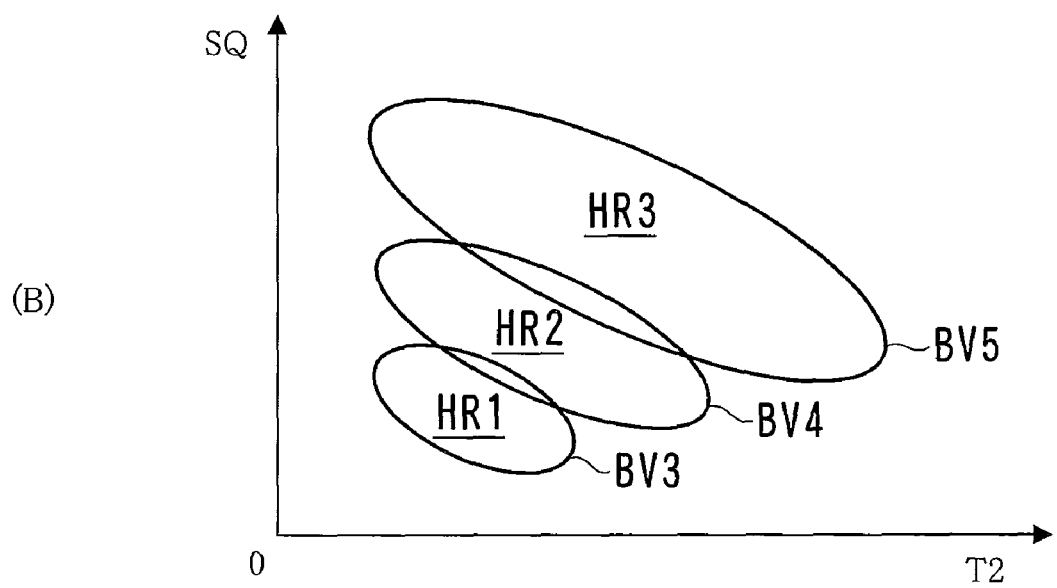

Note that in FIG. 11, although the curved lines BV1 and BV2 that are the boundaries for the areas HR1 to HR3 are defined by the straight lines connecting the points P, the coordinates of the points P can be coordinates other than those described above. Also, the number of points P can be increased. Furthermore, the curved lines can be defined by curved lines that pass through the points instead of straight lines that pass through the points P. Moreover, as shown in FIG. 14(A), the entirety of the curved lines BV1 and BV2 can each be defined by a single curved line. In this case, the curved lines BV1 and BV2 can be defined by expressions.

Also, as shown in FIG. 14(B), the areas HR1 to HR3 can be defined by closed curved lines BV3 to BV5.

The reference data DK obtained in this way is recorded in advance in the database DB1. The particle sizes, measurement time, and the like may be various values other than the values described above.

Note that examples of the reagent that can be used for such calibration include various sizes of polystyrene latex reference reagents manufactured by JSR Corporation. Also, ultrapure water that has been membrane processed can be used as the liquid ET.

Detection of Particle Sizes in Unknown Liquid ET

For an unknown liquid ET, measurement data DS is obtained by performing the same measurement (detection) as in the case of the reagents, and the size of particles included in the unknown liquid ET is detected with reference to the reference data DK.

For example, the number of dots in the areas HR1 to HR3 is obtained based on the area SQ and the peak time difference T2 from the measurement data DS. These numbers are compared with the reference data DK, the area ratio for each size in the reference data DK is referenced, and the numbers in the areas HR1 to HR3 indicated in the measurement data DS are assigned to the numbers in the areas HR1 to HR3 corresponding to the sizes. For each size, the numbers assigned to the respective areas HR1 to HR3 are added together to obtain a total number for each size. These total numbers are the numbers and sizes of particles detected in the unknown liquid ET.

Furthermore, by referencing the number concentration of the reagent for each size, the measurement time for the reagents and the unknown liquid ET, and the like, it is possible to obtain the number concentration for each size in the unknown liquid ET.

Also, by periodically acquiring the measurement data DS for the unknown liquid ET, it is possible to periodically detect the number concentration for each size. In this case, the measurement data DS obtained by measurement in each period may be considered to be one unit, and the sizes and numbers of particles in the liquid ET may be detected with use of measurement data DS pertaining to multiple units, such as 60 units. Then, in this case, by updating the measurement data DS by, for each period, adding one new unit as well as discarding an old unit, it is possible to detect the sizes and numbers of particles in the liquid ET in real-time for each period.

For example, by setting one period as 10 seconds, one unit as the measurement DS obtained by measuring for 10 seconds, and sequentially and consecutively performing measurement in the units, it is possible to detect the sizes and numbers of particles in the liquid ET in real-time every 10 seconds. This case is described later.

Additionally, by using the reference data DK, it is possible to detect the sizes and numbers of particles in the liquid ET from the measurement data DS by various techniques.

Description of Detection Circuit

Next is a description of a detection circuit 20.

Figure 3:
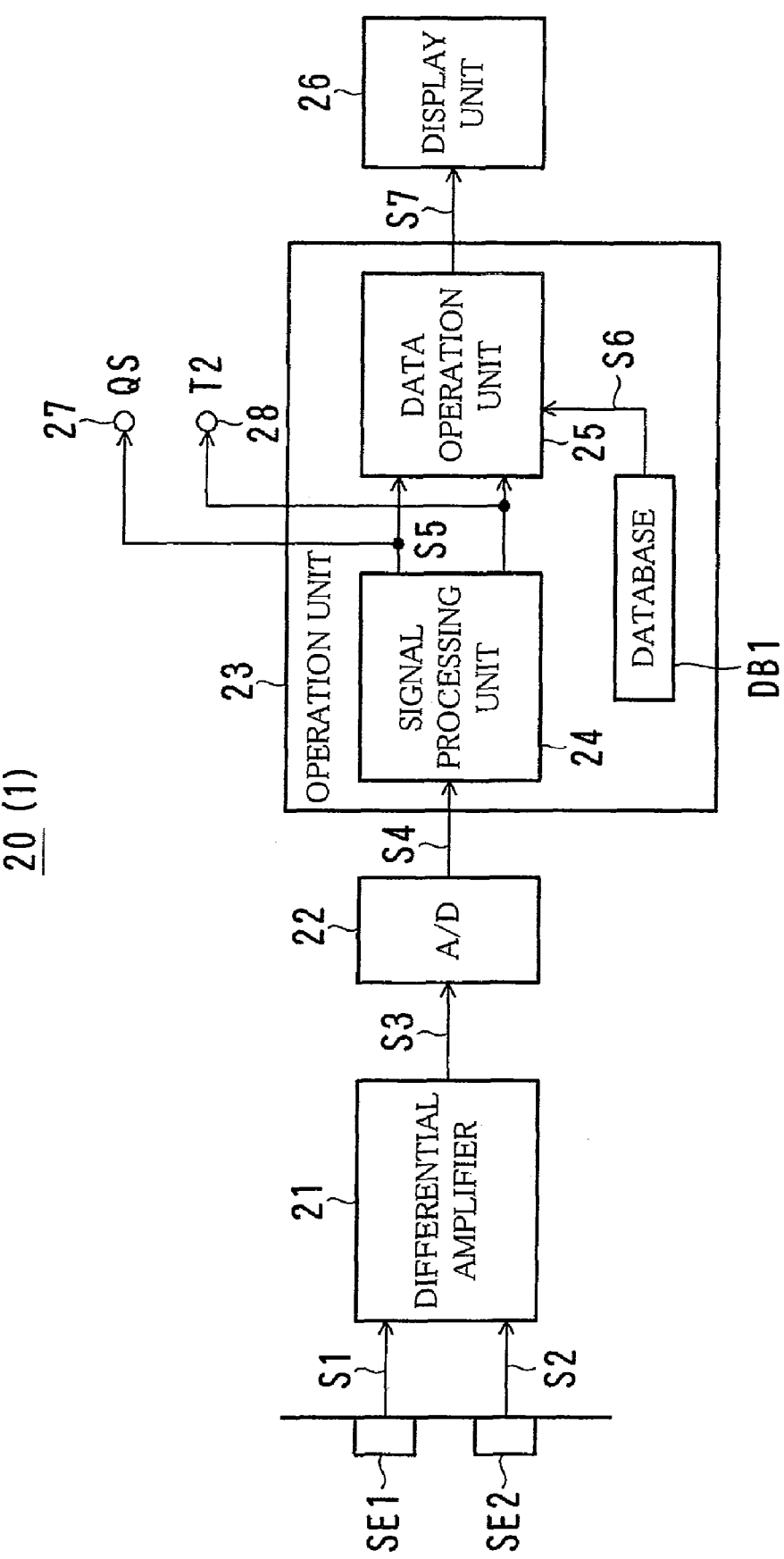
FIG. 3 is a block diagram showing an exemplary configuration of a detection circuit in the detection apparatus.

In FIG. 3, the output signals S1 and S2 from the light detection means SE1 and SE2 disposed parallel in the flow direction M1 of the liquid ET are differentially amplified by a differential amplifier 21 in order to raise the S/N ratio, thus becoming a signal S3 that is a voltage signal. At this time, either the output signal S2 or the output signal S1 is inverted and composited with the other one of the output signals S1 and S2. Accordingly, when the light detection means SE1 and SE2 are not detecting a diffraction fringe AM, the addition value of the output signals S1 and S2 cancel each other out and become zero output, and when a diffraction fringe AM has been detected, the output signals S1 and S2 rise.

The signal S3 output from the differential amplifier 21 is quantized by an AD converter 22, thus becoming a digital signal S4, which is input to an operation unit 23. In the operation unit 23, various operations or measuring is performed on the digital signal S4, and the size and number concentration NK of particles included in the liquid ET is output.

Specifically, in a signal processing unit 24, VPp, VPm, C1, C2, C3, and the like are obtained, the area SQ and the peak time difference T2 are obtained based on these, and the area SQ and the peak time difference T2 are stored in a memory as the measurement data DS. Furthermore, the reference data DK recorded in the database DB1 is referenced, and the size and number concentration NK of particles included in the liquid ET are obtained by a technique such as is described above.

Note that in the operation unit 23, the above-described VS, CS, CA, and the like can be set by a user, and the measurement data DS can be acquired based on such values that have been set by the user.

Also, the data indicating the area SQ and the peak time difference T2 is output to a T1 output terminal 27 and a T2 output terminal 28 respectively.

A calculated size KS and number concentration NK are displayed on the display face of a display unit 26. A signal S7 indicating the size KS and number concentration NK is output to an external device or the like. It is also possible for data indicating the number of particles assigned to the areas HR1 to HR3 for each size to be output to an external device.

The output to the external device can be output as serial data such as RS-232C. In this case, it is sufficient to, for example, serially output various data such as a measurement time, number in area HR1, number in area HR2, number in area HR3, and error messages.

One example of the output signal is shown below.
2008/08/30,19:32:45,00001070,00000032,00000006,0,0, 0,0,0, This kind of detection circuit 20 can be realized using a CPU or MPU, a RAM, a ROM, other peripheral devices, other hardware circuits, and the like. In particular, the operation unit 23 can be realized by the execution of a program stored in the ROM or the like by the CPU or MPU.

Also, the operation unit 23 in particular is easily realized with use of a personal computer. In this case, by processing the input digital signal S4 or signal S3 by a computer program, it is possible to perform the above-described operations and output the signal S7.

Also, based on the signals output from the detection apparatus 1, the size KS and number concentration NK may be calculated with use of a personal computer, and furthermore the result thereof may be displayed.

Effects of the Detection Apparatus 1 of the Present Embodiment

In this way, according to the present embodiment, based on merely an observed signal, it is possible to directly detect the size of the particle on which the signal is based. Specifically, a correlation unique to each particle size arises between the area SQ and the peak time difference T2, and by merely specifying the area SQ and the peak time difference T2 by using these correlation functions, it is possible to easily and directly obtain the size of a particle on which the area SQ and peak time difference T2 are based.

Also, in the case of applying the present embodiment, the measurement error is the same in each section "a", "b", and "c" in Patent Document 1, and there is no accumulation of error from a large particle section to a small particle section, thus improving reliability. Since statistical processing is unnecessary, there is a reduction in the time from the start of measurement until the first display. Since discrimination based on merely a signal is possible, measurement is possible even if the size of the particle is small.

As described above, in the present embodiment, two light detection means (light receiving elements) SE are disposed as a pair horizontally in the flow direction M1 of the liquid (water sample) ET. However, this configuration is for indicating the method and principle of measurement, and in an actual apparatus, it is preferable to increase the number of pairs with use of a photodiode array or the like, and increase the active light receiving area. Also, a light receiving element that can perform image processing, such as a CCD, may be disposed.

The detection apparatus 1 described above can perform constant monitoring by performing inline connection, is easy to handle and highly maintainable, and can be provided at low cost.

Specific Example of Calculation of Number Concentration NK

The following describes a specific example of calculation performed to obtain the size and number concentration NK of particles included in the liquid ET based on the measurement data DS.

FIG. 15 is a diagram showing an example of the reference data DK1, FIG. 16 is a diagram showing an example of the measurement data DS1, and FIGS. 17 to 21 are diagrams showing calculation progression.

First, in a calibration operation, measurement was performed using three kinds of stand-alone reagents whose particle sizes are 400 nm, 300 nm, and 200 nm by the detection apparatus 1, thus obtaining the reference data DK1 shown in FIG. 15.

In FIG. 15, the number concentration NK of the 400 nm, 300 nm, and 200 nm reagents was 1,000, 2,000, and 5,000 (pls/ml) respectively. The measurement time was 10 minutes. The unit (pls/10 min) in the areas HR1 to HR3 shows the number of pulses, that is to say, the number of particles obtained by measurement for 10 minutes.

Next, the liquid ET whose particle number concentration NK is unknown was measured with use of the same detection apparatus 1, thus obtaining the measurement data DS1 shown in FIG. 16.

In FIG. 16, the total number of measured particles is 4,150, 1,370 of which were assigned to area 3, 1,610 of which were assigned to area 2, and 1,170 of which were assigned to area 1. The measurement time was the same 10 minutes.

In FIG. 16, the issue is obtaining values for the places indicated by question marks, and ultimately, the issue is obtaining the number concentration NK for each size.

First is $X1abc=X1a+X1b+X1c$.

Here, $X1c$ (number of 200-nm particles in area 1) and $X2c$ (number of 200-nm particles in area 2) are assumed to be 0.

In order to obtain the number of 400-nm particles in the areas HR1 to HR3, $X1abc$ is distributed between $X1a$ and $X1b$.

$$X1a=X1abc \times (P2b/P1b-X2abc/X1abc)/(P2b/P1b-P2a/P1a)=1170 \times (2500/800-1610/1170)/(2500/800-700/2500)=719.2$$

In other words, in accordance with the proportion obtained from the numerical values and the like indicated by the reference data DK, the 1,170 particles ($X1abc$) assigned to area 1 in the measurement data DS1 is distributed between the number in area 1 for the 400-nm particles ($X1a$) and the number in area 1 for the 300-nm particles ($X1b$) by proportional distribution.

The values of Xa2 and Xa3 are obtained from the obtained value of X1a.

$$X2a = X1a \times P2a/P1a$$
$$= 719.2 \times 700/2500$$
$$= 201.4$$

$$X3a = X1a \times P3a/P1a$$
$$= 719.2 \times 300/2500$$
$$= 86.3$$

Next, as shown in FIG. 17, the numbers of 400-nm particles in the areas HR are subtracted from the first numbers of particles in the areas HR in the measurement data DS1.

Then, in order to obtain the numbers of 300-nm particles in the areas HR1 to HR3, X2bc is distributed between X2b and X2c.

$$X2b = X2bc \times (P3c/P2c - X3bc/X2bc)/(P3c/P2c - P3b/P2b)$$
$$= 1408.6 \times \left(\begin{array}{c} 2000/800 - \\ 1283.7/1408.6 \end{array}\right) / \left(\begin{array}{c} 2000/800 - \\ 700/2500 \end{array}\right)$$
$$= 1008.0$$

The value of X3b is obtained from the value of X2b.

$$X3b = X2b \times P3b/P2b$$
$$= 1008.0 \times 700/2500$$
$$= 282.2$$

The value of X3c is obtained $$X3c = X3bc - X3b$$
$$= 1283.7 - 282.2$$
$$= 1001.5$$

The values of X1c and X2c that were assumed to be 0 at first are obtained from the value of X3c.

$$X1c = X3c \times P1c/P3c$$
$$= 1001.5 \times 200/200$$
$$= 100.1$$

$$X2c = X3c \times P2c/P3c$$
$$= 1001.5 \times 800/200$$
$$= 400.6$$

The condition for assuming a value of 0 at first is canceled. Accordingly, the values of X1c and X2c are changed as shown in FIG. 18.

The obtained numbers of 200-nm particles in the areas HR are subtracted from the first numbers of particles in the areas HR in the measurement data DS1. Accordingly, the resulting values of X2ab and X1ab are as shown in FIG. 19.

In order to re-obtain the numbers of 400-nm particles in the areas HR1 to HR3, X1ab is distributed between X1a and X1b.

$$X1a = X1ab \times \left(\begin{array}{c} P2b/P1b - \\ X2abc/X1abc \end{array}\right) / (P2b/P1b - P2a/P1a)$$
$$= 1069.9 \times (2500/800 - 1610/1170)/(2500/800 - 700/2500)$$
$$= 750.1$$

The values of X2a and X3a are obtained from the value of X1a.

$$X2a = X1a \times P2a/P1a$$
$$= 750.1 \times 700/2500$$
$$= 210.0$$

$$X3a = X1a \times P3a/P1a$$
$$= 750.1 \times 300/2500$$
$$= 90.0$$

As shown in FIG. 20, the obtained numbers of 400-nm particles in the areas HR are subtracted from the first numbers of particles in the areas HR in the measurement data DS.

In order to obtain the numbers of 300-nm particles in the areas HR1 to HR3, X2bc is distributed between X2b and X2c.

$$X2b = X2bc \times (P3c/P2c - X3bc/X2bc)/(P3c/P2c - P3b/P2b)$$
$$= 1400 \times \left(\begin{array}{c} 2000/800 - \\ 1283.7/1408.6 \end{array}\right) / (2000/800 - 700/2500)$$
$$= 1000.0$$

The value of X3b is obtained from the value of X2b.

$$X3b = X2b \times P3b/P2b$$
$$= 1000 \times 700/2500$$
$$= 280.0$$

The value of X3c is obtained.

$$X3c = X3bc - X3b$$
$$= 1280 - 280$$
$$= 1000.0$$

The number concentration NK for each size, that is to say, XNa, XNb, and XNc are calculated based on these calculation results.

$$XNa = X123a \times Na/X123a$$
$$= 1050.1 \times 1000/3500$$
$$= 300.0$$

$$XNb = X123b \times Nb/X123b$$
$$= 1600 \times 2000/4000$$
$$= 800.0$$

$$XNc = X123c \times Nc/X123C$$
$$= 1500 \times 5000/3000$$
$$= 2500.0$$

The places indicated by question marks in FIG. 16 are filled in based on these calculation results. The results are shown in FIG. 21.

Specifically, the number concentrations XNa, XNb, and XNc for the 400-nm particles, 300-nm particles, and 200-nm particles are 300.0, 800.0, and 2,500.0 (pls/ml).

Evaluation of Linearity of Measurement by Detection Apparatus 1

In order to evaluate the linearity of the measurement by the detection apparatus 1, the input amounts of 200-nm particle, 300-nm particle, and 400-nm particle reagents were varied, and the input amounts and corresponding detection results were compared.

As a result, the linearity was favorable in each case. The following shows experimentation results for the 200-nm particle reagent. Substantially the same results were obtained for both the 200-nm particle and 400-nm particle reagents.

Figure 23:
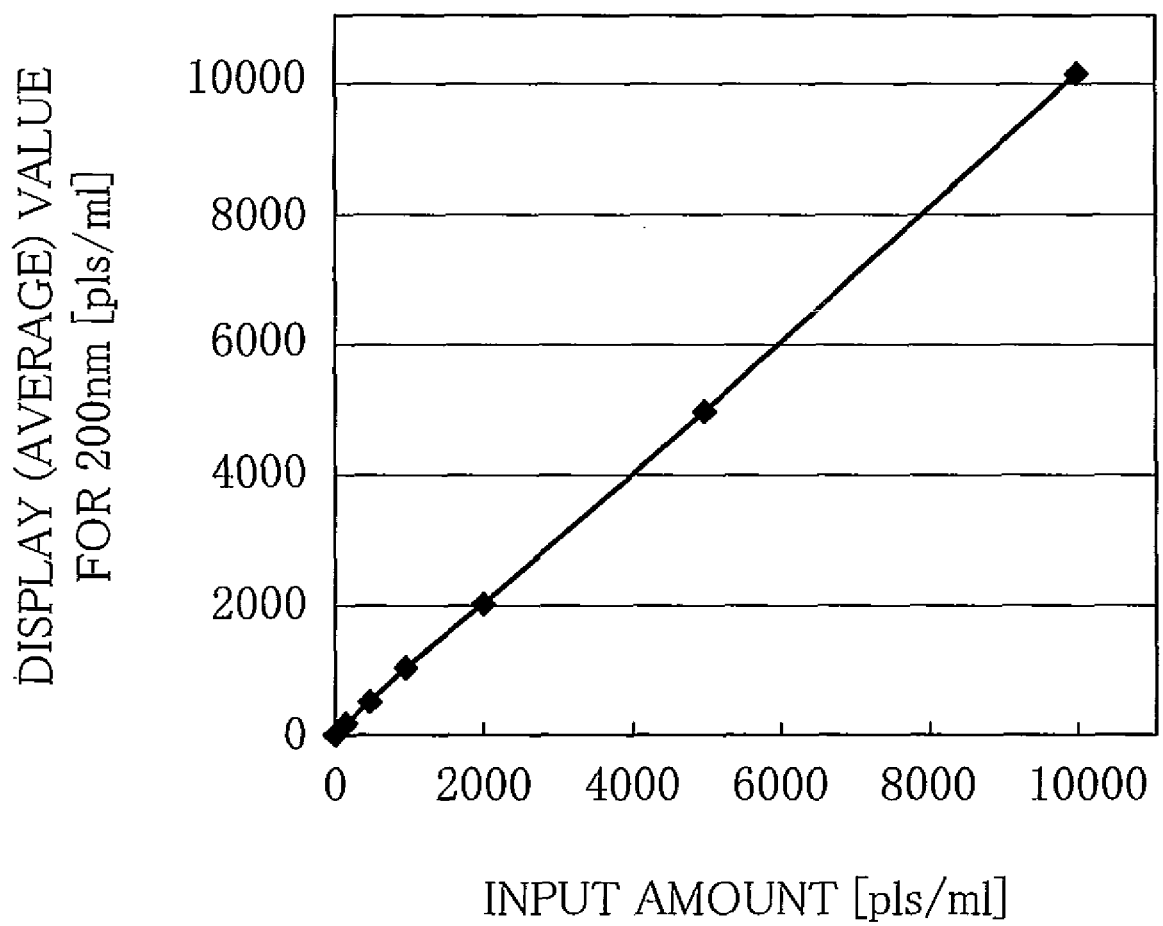
FIG. 23 is a graph showing the experimentation results of FIG. 22.

FIG. 22 is a diagram showing input amounts for the 200-nm particle reagent and the number of particles for each size obtained by measurement, and FIG. 23 shows graphs showing the experimentation results of FIG. 22.

As shown in FIG. 22, values measured for the 200-nm particle number concentrations NK were substantially the same as the input amounts. Also, as the input amount increased, the 200-nm particle number concentration NK that was measured also increased.

As shown in FIG. 23, when plotted, the relationship between the input amount of the 200-nm particle reagent and the 200-nm particle number concentration NK that was measured was on a substantially straight line. Accordingly, it was found that the linearity in each case was favorable.

Example of Measurement Timing

Next is a description of an example of timings at which the detection apparatus 1 performs measurement on an unknown liquid ET.

Here, as described above, the measurement data DS is periodically acquired and set as one unit, and 60 units worth of the measurement data DS is accumulated. Also, for each period, the oldest unit is updated with a newly obtained unit.

FIG. 24 is a diagram showing 60 units of accumulated measurement data.

In FIG. 24, each unit is the measurement DS obtained by measuring for 10 seconds, and based on this, the particle numbers A, B, and C in the areas HR1 to HR3 are shown. The particle numbers ΣA, ΣB, and ΣC in the areas HR1 to HR3 measured for 10 minutes are obtained by calculating the total of the 60 units worth of measurement data. The data of the unit obtained by measuring 10 seconds later, that is to say, in the next period is added, and the data of the oldest unit is discarded. Accordingly, a newest particle numbers ΣA, ΣB, and ΣC are obtained every 10 seconds. Based on this, the sizes and numbers of particles in the liquid ET can be detected in real-time.

In other words, the detection apparatus 1 measures the peak time difference T2 and the area SQ, for example, each time a particle is detected. Based on this, the detected particle is assigned to one of the areas HR1 to HR3, and the number counter corresponding to the area HR1 to HR3 to which the particle was assigned is incremented.

The number counters corresponding to the areas HR1 to HR3 output their count value every 10 seconds, and the output count values are stored in a memory as one unit of data. Once measurement has started, this processing is repeated until 60 units worth of data has been accumulated.

Furthermore, when the 61st unit is output 10 seconds later, the 1st unit is discarded, the 61st unit is added, a new sum of 60 units worth of data is obtained, and furthermore, the number concentration NK for each size is calculated based on the new sum.

According to this kind of measurement method, the number concentration NK calculated for each size is based on the measurement from the past 10 minutes, and regardless of being superior in terms of reliability, measurement results are obtained every 10 seconds, and therefore the user does not need to wait 10 minutes for measurement results, and this measurement method is superior in terms of real-time ability.

Also, by comparing the particle number in the areas HR1 to HR3 for the past 10 minutes, past 5 minutes, past 1 minute, and the like, it is possible to estimate the particle number in the areas HR1 to HR3 for 10 minutes later. Accordingly, it is also possible to predict or promptly detect the occurrence of an emergency such as a membrane breakage in the flow channel of the liquid ET, and handle the emergency.

Specifically, if membrane breakage occurred, several tens of thousands of times the number of microparticles before the breakage would flow at once, the semiconductor manufacturing apparatus and the like would become contaminated, and a long time would be required for restoration, and it is possible to predict or promptly detect the occurrence of such an emergency, and handle it.

Note that the measurement data DS obtained by measuring every 10 seconds can be used as a water condition indicator. Specifically, based on the measurement data DS, it is possible to manage the condition of the liquid ET, that is to say, the condition of the size of particles included in the liquid ET. In this case, instead of obtaining the number concentration NK for each size of particle included in the liquid ET by calculation, the measurement data DS itself is used as the detected values of the sizes of particles included in the liquid ET.

Description Using a Flowchart

Figure 25:
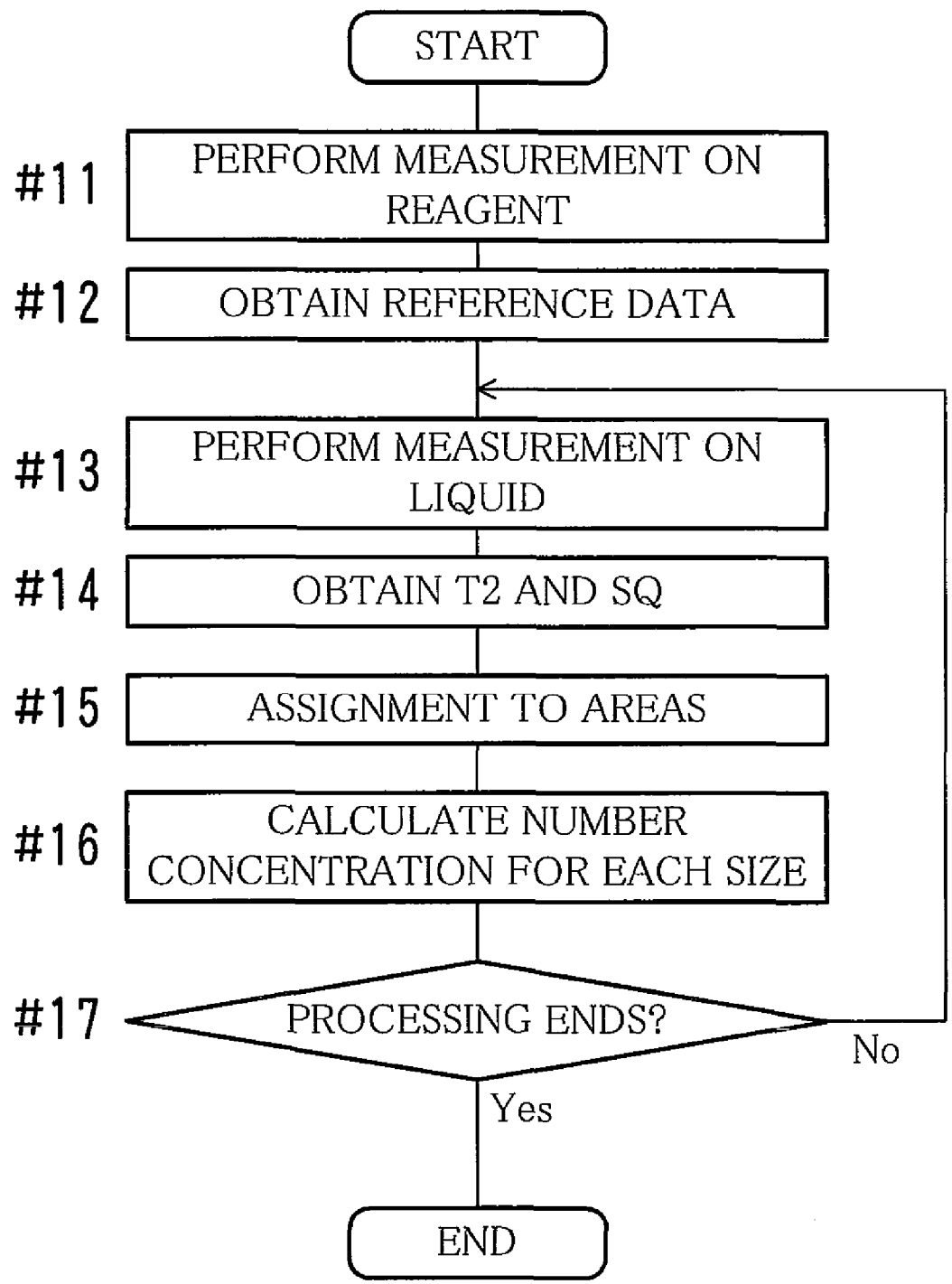
FIG. 25 is a flowchart showing a number concentration detection operation performed in the detection apparatus.
Figure 26:
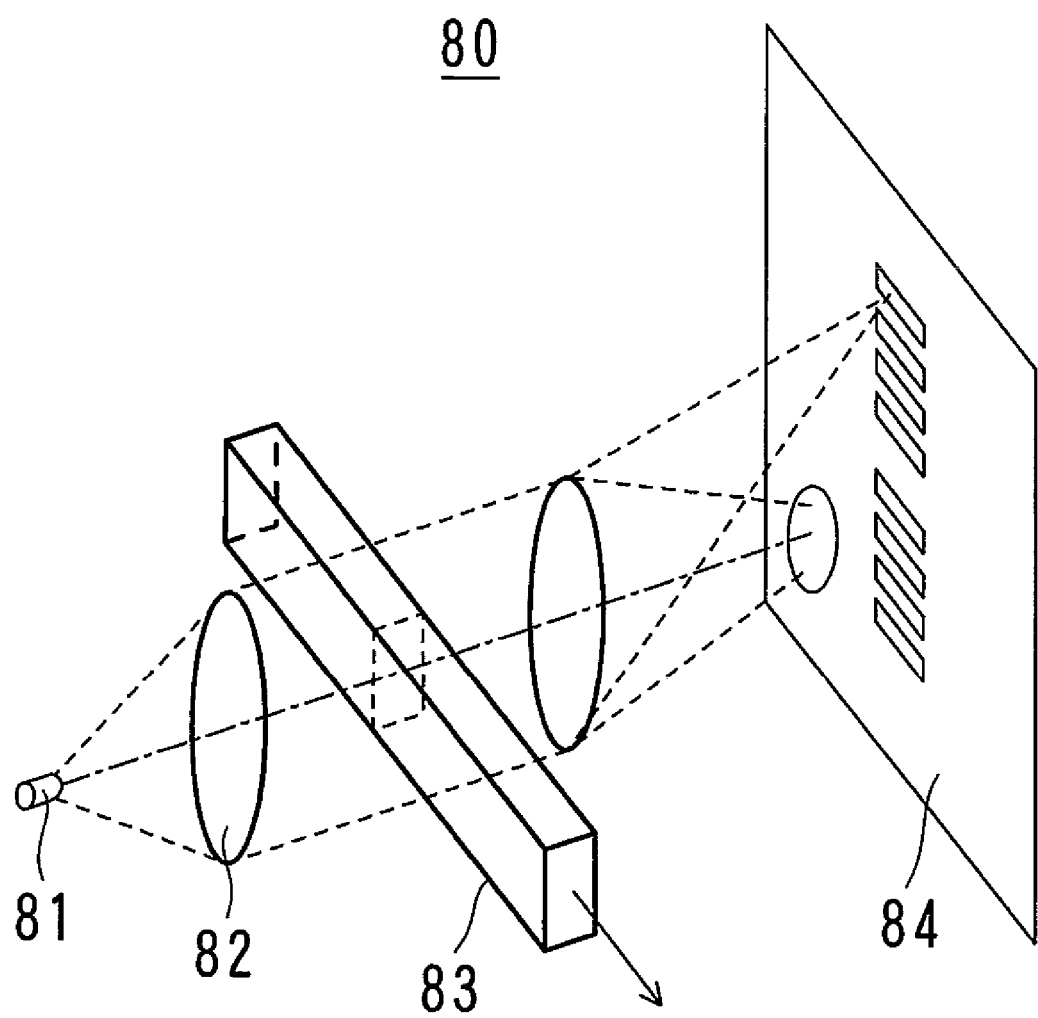
FIG. 26 is a diagram showing a configuration of a conventional scattered light-type detection apparatus.

FIG. 25 is a flowchart showing operations for detecting a particle number concentration NK in the detection apparatus 1.

In FIG. 25, measurement is performed using a reagent (#11), and the reference data DK is obtained (#12). Measurement is performed for an unknown liquid ET (#13), and the peak time difference T2 and the area SQ for each diffraction fringe AM are obtained (#14). Assignment to the areas HR1 to HR3 is performed (#15), and the number concentration NK for each size is calculated based on the result of the assignment (#16). The processing from step #13 onward is repeated until detection processing ends (#17).

Other Embodiments

Although there are three areas HR in the embodiment described above, there may be four or more areas. Although the detected sizes are 200, 300, and 400 nm, it is possible to think that, for example, 200 is 250 or less, 300 is 250 to 350, and 400 is 350 or more. Also, other sizes may be used.

Also, as long as the object is chronologically and relatively finding out the condition of an unknown liquid ET in measuring, it is possible to set the display value to be a value obtained by summing the number counts in the areas indicated in the measurement data DS at an arbitrary time without obtaining the number concentrations NK.

In the embodiment described above, the configuration, structure, shape, dimensions, number, and material of part or the entirety of the laser light source 11, the lens 13, the tube channel KR, the light detection means SE, the detection circuit 20, the database DB1, and the detection apparatus 1, as well as the method of calculating the area SQ, the method of calculating the number concentration NK for each size from the area SQ and peak value VP, the content and sequence of the processing, and the like can be appropriately changed in conformity with the spirit of the present invention.

The invention claimed is:

1. A method of detecting a size of particles in a liquid by irradiating a tube channel having translucency with coherent light such that the light traverses a flow direction of a liquid flowing in the tube channel, and detecting diffraction fringes that appear due to the particles included in the liquid by a light detection portion, a first light detection portion and a second light detection portion being provided as the light detection portion, and the second light detection portion being provided so as to be separated from the first light detection portion by a predetermined distance farther downstream along the flow direction of the liquid than the first light detection portion, and the method comprising the steps of:

measuring, for each diffraction fringe detected in a predetermined time period by the first light detection portion and the second light detection portion, a peak time difference T2 that is a difference between times at which peak values appear in a detection signal from the first light detection portion and the second light detection portion, and an area SQ based on the waveform of the detection signal; and detecting a size of the particles included in the liquid based on the peak time differences T2 and the areas SQ that were measured.

2. The method of detecting a size of particles in the liquid according to claim 1, comprising the step of:

obtaining reference data in advance by performing actual measurement with use of a sample solution, and recording the reference data in a database, the reference data indicating, for a plurality of particle sizes, a relationship between each size and the peak time difference T2 and the area SQ that correspond to the size, wherein a size of the particles included in the liquid is detected with reference to the database.

3. The method of detecting a size of particles in the liquid according to claim 2, comprising the steps of:

defining, in advance in a coordinate plane in which the peak time difference T2 is the x axis and the area SQ is the y axis, a plurality of areas for assignment of the diffraction fringes in accordance with the particle sizes;

obtaining reference data in advance by performing actual measurement with use of the sample solution, and recording the reference data in the database, the reference data indicating, for the plurality of particle sizes, a relationship between each size and the number or proportion of diffraction fringes included in each of the plurality of areas;

acquiring actual measurement data that indicates the number of diffraction fringes assigned to each of the plurality of areas based on the peak time differences T2 and the areas SQ that were measured; and detecting the number or proportion corresponding to each size of the particles included in the liquid with use of the reference data and the actual measurement data.

4. The method of detecting a size of particles in the liquid according to claim 3, wherein the number corresponding to each size of the particles included in the liquid is detected by distributing the number of diffraction fringes indicated in the actual measurement data among the plurality of areas for each size by performing a simulation with reference to the reference data.

5. The method of detecting a size of particles in the liquid according to claim 2, wherein the area SQ is obtained by approximation with a triangle whose base is a duration of a waveform in the detection signal and whose height is the peak value of the waveform.

6. The method of detecting a size of particles in the liquid according to claim 5, wherein radiant light whose focal point is in the liquid is used as the light.

7. The method of detecting a size of particles in the liquid according to claim 6, wherein the first light detection portion and the second light detection portion have been disposed so as to receive, among a range in which the radiant light is projected, an entire range in the right angle direction relative to the flow direction of the liquid at positions of the respective light detection portion.

8. An apparatus that detects a size of particles in a liquid by irradiating a tube channel having translucency with coherent light such that the light traverses a flow direction of a liquid flowing in the tube channel, and detecting diffraction fringes that appear due to the particles included in the liquid by a light detection portion, the apparatus comprising:

a first light detection portion for detecting the diffraction fringes;

a second light detection portion provided so as to be separated from the first light detection portion by a predetermined distance farther downstream along the flow direction of the liquid than the first light detection portion;

a time difference measurement portion for measuring, for each diffraction fringe detected in a predetermined time period by the first light detection portion and the second light detection portion, a peak time difference T2 that is a difference between times at which peak values appear in a detection signal from the first light detection portion and the second light detection portion;

an area measurement portion for measuring, for each of the diffraction fringes, an area SQ based on a waveform of the detection signal; and a size detection portion for detecting a size of the particles included in the liquid based on the peak time differences T2 and the areas SQ that were measured.

9. The apparatus that detects a size of particles in the liquid according to claim 8, comprising:

a database having recorded therein reference data obtained in advance by performing actual measurement with use of a sample solution, the reference data indicating, for a plurality of particle sizes, a relationship between each size and the peak time difference T2 and the area SQ that correspond to the size, wherein the size detection unit detects a size of the particles included in the liquid with reference to the database.

10. The apparatus that detects a size of particles in the liquid according to claim 9, comprising:

a definition memory having stored therein definition data that defines, in a coordinate plane in which the peak time difference T2 is the x axis and the area SQ is the y axis, a plurality of areas for assignment of the diffraction fringes in accordance with the particle sizes;

a database having recorded therein reference data obtained in advance by performing actual measurement with use of the sample solution, the reference data indicating, for the plurality of particle sizes, a relationship between each size and the number or proportion of diffraction fringes included in each of the plurality of areas;

an actual measurement data acquisition portion for acquiring actual measurement data that indicates the number of diffraction fringes assigned to each of the plurality of areas based on the peak time differences T2 and the areas SQ that were measured; and a size detection portion for detecting the number or proportion corresponding to each size of the particles included in the liquid with use of the reference data and the actual measurement data.

11. The apparatus that detects a size of particles in the liquid according to claim 10, wherein the size detection portion detects the number corresponding to each size of the particles included in the liquid by distributing the number of diffraction fringes indicated in the actual measurement data among the plurality of areas for each size by performing a simulation with reference to the reference data.

12. The apparatus that detects a size of particles in the liquid according to claim 9, wherein the area measurement portion obtains the area SQ by approximation with a triangle whose base is a duration of a waveform in the detection signal and whose height is the peak value of the waveform.

13. The apparatus that detects a size of particles in the liquid according to claim 12, wherein radiant light whose focal point is in the liquid is used as the light, and the first light detection portion and the second light detection portion have been disposed so as to receive, among a range in which the radiant light is projected, an entire range in the right angle direction relative to the flow direction of the liquid at positions of the respective light detection portion.

14. The apparatus that detects a size of particles in the liquid according to claim 13, wherein the first light detection portion and the second light detection portion are a light receiving element such as a photodiode or a photodiode transistor.

15. The method of detecting a size of particles in the liquid according to claim 3, wherein the area SQ is obtained by approximation with a triangle whose base is a duration of a waveform in the detection signal and whose height is the peak value of the waveform.

16. The method of detecting a size of particles in the liquid according to claim 4, wherein the area SQ is obtained by approximation with a triangle whose base is a duration of a waveform in the detection signal and whose height is the peak value of the waveform.

17. The apparatus that detects a size of particles in the liquid according to claim 10, wherein the area measurement portion obtains the area SQ by approximation with a triangle whose base is a duration of a waveform in the detection signal and whose height is the peak value of the waveform.

18. The apparatus that detects a size of particles in the liquid according to claim 11, wherein the area measurement portion obtains the area SQ by approximation with a triangle whose base is a duration of a waveform in the detection signal and whose height is the peak value of the waveform.

* * * * *